US010165955B2

(12) United States Patent
Gladshtein et al.

(10) Patent No.: US 10,165,955 B2
(45) Date of Patent: Jan. 1, 2019

(54) OBTAINING CARDIOVASCULAR PARAMETERS USING ARTERIOLES RELATED TRANSIENT TIME

(71) Applicant: VITA-SENTRY LTD., Netanya (IL)

(72) Inventors: Reuven Gladshtein, Netanya (IL); Eilon Rahman, Netanya (IL)

(73) Assignees: Reuven Gladshtein, Netanya (IL); Eilon Rahman, Netanya (IL)

( * ) Notice: Subject to any disclaimer, the term of this patent is extended or adjusted under 35 U.S.C. 154(b) by 29 days.

(21) Appl. No.: 14/612,695

(22) Filed: Feb. 3, 2015

(65) Prior Publication Data

US 2016/0367154 A1 Dec. 22, 2016

Related U.S. Application Data

(60) Provisional application No. 61/936,805, filed on Feb. 6, 2014.

(51) Int. Cl.
*A61B 5/00* (2006.01)
*A61B 5/02* (2006.01)
*A61B 5/026* (2006.01)
*A61B 3/12* (2006.01)
*A61B 5/1455* (2006.01)
(Continued)

(52) U.S. Cl.
CPC .......... *A61B 5/0261* (2013.01); *A61B 3/1233* (2013.01); *A61B 3/1241* (2013.01); *A61B 5/02007* (2013.01); *A61B 5/0245* (2013.01); *A61B 5/02416* (2013.01); *A61B 5/02438* (2013.01); *A61B 5/14555* (2013.01); *A61B 5/14556* (2013.01); *A61B 5/6821* (2013.01); *A61B 5/6823* (2013.01); *A61B 5/6824* (2013.01); *A61B 2560/0431* (2013.01)

(58) Field of Classification Search
CPC ............ A61B 5/02007; A61B 5/02416; A61B 5/02438; A61B 5/0245; A61B 5/0261; A61B 3/1233; A61B 3/1241
USPC ........................................................ 600/479
See application file for complete search history.

(56) References Cited

U.S. PATENT DOCUMENTS 4,562,843 A     1/1986  Djordjevich et al.
5,778,878 A *   7/1998  Kellam ................ A61B 5/0261
                                                     600/310

(Continued)

FOREIGN PATENT DOCUMENTS

EP         1297784       4/2003
WO       2007097702      2/2007

(Continued)

OTHER PUBLICATIONS

Non-Invasive Techniques for Assessment of Peripheral Blood Flow at Different Vascular Depths in Mälardalen University Press Licentiate Theses No. 131,Copyright © Jimmie Hagblad, 2011 ISBN 978-91-7485-014-7 ISSN 1651-9256 Printed by Mälardalen University, Västerås, Sweden.

(Continued)

*Primary Examiner* — Christopher A Flory
(74) *Attorney, Agent, or Firm* — Mark M. Friedman

(57) ABSTRACT

Methods for monitoring equivalent inner diameter of arterioles by measuring blood pressure wave transient time from small arteries to arterioles and calculating, from the transient time and concurrently measured heart rate values, an equivalent inner diameter of arterioles.

15 Claims, 19 Drawing Sheets

(51) Int. Cl.
*A61B 5/024* (2006.01)
*A61B 5/0245* (2006.01)

(56) References Cited

U.S. PATENT DOCUMENTS

| | | | |
|---|---|---|---|
| 5,891,022 | A | 6/1999 | Pologe |
| 6,123,719 | A | 9/2000 | Masychev |
| 6,549,801 | B1* | 4/2003 | Chen ................. A61B 5/0073 250/350 |
| 6,859,658 | B1 | 2/2005 | Krug |
| 7,481,772 | B2 | 1/2009 | Banet |
| 7,736,311 | B2 | 6/2010 | Bartnik et al. |
| 2003/0135124 | A1* | 7/2003 | Russell ............. A61B 5/02007 600/500 |
| 2004/0186369 | A1* | 9/2004 | Lam ...................... G06T 3/0062 600/407 |
| 2005/0222514 | A1 | 10/2005 | Sugo et al. |
| 2006/0224058 | A1* | 10/2006 | Mannheimer ...... A61B 5/14552 600/323 |
| 2006/0235669 | A1* | 10/2006 | Charbel ................ G06F 19/321 703/11 |
| 2007/0225614 | A1* | 9/2007 | Naghavi .................. A61B 5/01 600/549 |
| 2008/0015451 | A1 | 1/2008 | Hatib et al. |
| 2008/0241199 | A1* | 10/2008 | Silverman ............ A61B 5/0261 424/400 |
| 2010/0049007 | A1* | 2/2010 | Sterling ............. A61B 5/14552 600/301 |
| 2010/0049023 | A1* | 2/2010 | Sterling ............. A61B 5/14551 600/363 |
| 2010/0081941 | A1 | 4/2010 | Haghavi et al. |
| 2010/0298222 | A1* | 11/2010 | Dewhirst ................ A61K 31/21 514/13.5 |
| 2010/0331708 | A1 | 12/2010 | Hatib |
| 2011/0048556 | A1* | 3/2011 | Carter .................. F16K 31/122 137/559 |
| 2013/0171599 | A1* | 7/2013 | Bleich .................. A61B 5/0456 434/247 |
| 2013/0204169 | A1* | 8/2013 | Poepperling ....... A61H 23/0263 601/46 |
| 2013/0317368 | A1* | 11/2013 | Warren ................ A61B 5/0075 600/473 |
| 2013/0317373 | A1* | 11/2013 | Warren ................ A61B 5/0075 600/479 |
| 2013/0324866 | A1* | 12/2013 | Gladshtein ........... A61B 5/0059 600/507 |
| 2013/0338462 | A1* | 12/2013 | Warren ................ A61B 5/0075 600/328 |
| 2013/0338511 | A1* | 12/2013 | Warren ................ A61B 5/0075 600/479 |
| 2013/0338512 | A1* | 12/2013 | Warren ................ A61B 5/0075 600/479 |
| 2014/0027293 | A1* | 1/2014 | Lu ........................... B23P 15/24 205/70 |
| 2014/0058232 | A1* | 2/2014 | Andrijauskas ..... A61B 5/14546 600/328 |
| 2014/0268163 | A1* | 9/2014 | Milner .................... A61B 3/102 356/451 |
| 2015/0190090 | A1* | 7/2015 | Silverman .............. A61K 31/04 600/363 |
| 2015/0216425 | A1* | 8/2015 | Gladshtein ........... A61B 3/1233 600/431 |
| 2016/0220129 | A1* | 8/2016 | Ostroverkhov ...... A61B 5/0261 |
| 2016/0249812 | A1* | 9/2016 | Wang ................... A61B 5/0059 600/407 |
| 2016/0310053 | A1* | 10/2016 | Warren ................ A61B 5/0075 |
| 2017/0027444 | A1* | 2/2017 | Rege ..................... A61B 3/0008 |

FOREIGN PATENT DOCUMENTS

| | | |
|---|---|---|
| WO | 2010057485 | 5/2010 |
| WO | 2010057495 A2 | 5/2010 |
| WO | 20110048556 | 4/2011 |
| WO | 2011066546 | 6/2011 |
| WO | 2012110955 | 8/2013 |
| WO | 20140027293 | 2/2014 |

OTHER PUBLICATIONS

Takanori Igarashi?, Ko Nishino†, and Shree K. Nayar :The Appearance of Human Skin—Technical Report CUCS-024-05 Department of Computer Science, Columbia University, New York, NY 10027, USA Jun. 2005.

J. Hagblad • L.-G. Lindberg • A. Kaisdotter Andersson •S. Bergstrand • M. Lindgren—A.-C. Ek • M. Folke • M. Linde 'n "A technique based on laser Doppler flowmetry and photoplethysmography for simultaneously monitoring blood flow at different tissue depth"—published in Med Biol Eng Comput (2010) 48:415-422 DOI 10.1007/s11517-010-0577-2.

Editor in CHief R. G. Vaila ; IADVL Textbook and Atlas of Tematology, vol. 1 second Edition,(few pages re Structure of the skin), Copyright © 2001 Bhalani Publishing House, Mumbai.

R. S. Chadwick; "Pulse-wave propagation in an artery with leakage into small side branches" in Proc. Natl. Acad. Sci. USA vol. 82, pp. 5237-5241, Aug. 1985 Applied Mathematical Sciences.

A. Douplik et al: "In Vivo Real Time Monitoring of Vasoconstriction and Vasodilation by a Combined Diffuse Reflectance Spectroscopy and Doppler Optical Choherences Tomography Approach", published in Laser in Surgery and Medicine 40:323-331 (2008).

Phillipe Reymond et al ; "Validation of a one-dimensional model of the systemic arterial tree", published in Am J Physiol Heart Circ Physiol 297: H208-H222, 2009. First published May 8, 2009; doi:10.1152/ajpheart.00037.2009.

John A. Adam; "Blood Vessel Branching: beyond the Standard Calculus Problem", Mathematics Magazine.84 ( 2011) pp. 196-201.

A.C. Fowler et al; "A Delay Recruitment Model of the Cardiovascular Control System", Journal of Mathematical Biology Nov. 2005, vol. 51, Issue 5, pp. 508-526.

Hs Lim and Gyh Lip; "Arterial Stiffness in Diabetes and Hypertension", Journal of Human Hypertension (2004) 18, 487-468. doi:10.1038/sj.jhh. 1001693 , Published online Feb. 26, 2004.

John Allen: "Photoplethysmography and its Application in Clinical Physiological Measurement", Physiol. Meas. 28 (2007) R1-R39.

Josep Sola et al; " Ambulatory Monitoring of the Cardiovascular System: The Role of PulseWave Velocity", New Developments in Biomedical Engineering Edited by Domenico Campolo, Publisher InTech Published online Jan. 1, 2010, Published in print edition Jan. 2010.

Emilie Franceschini et al, "Ultrasound characterization of red blood cells distribution: a wave scattering simulation study" , Journal of Physics: Conference Series 269 (2011) 012014.

Minan Xu, "Local measurement of the Pulse Wave Velocity Using Doppler Ultrasound", can be read in http://dspace.mit.edu/bitstream/handle/1721.1/16868/51677789.pdf.

Estimation of local pulse wave velocity using arterial diameter waveforms: Experimental validation in sheep, by S Graf1,3,4. D Craiem1,3, J G Barra1,2 and R L Armentano1 ; Published under licence by IOP Publishing Ltd Journal of Physics: Conference Series, vol. 332, conference 1.

Joseph B Mandeville, John J A Marota, C Ayata, Greg Zaharchuk, Michael A Moskowitz, Bruce R Rosen, and Robert M Weisskoff, "Evidence of a Cerebrovascular Postarteriole Windkessel With Delayed Compliance", Journal of Cerebral Blood Flow & Metabolism (1999) 19, 679-689.

J. Keener and J. Sneyd, "Mathematical Physiology", vol. 8th of Interdisciplinary Applied Mathematics New York, NY: Springer Verlag, 1998. http://www.google.co.il/url?q=http://www.fulviofrisone.com/attachments/article/412/mathematical%2520physiology.pdf&sa=U&ved=0ahUKEwjOoP3Wj9LWAhWHuBoKHZISDrkQFggTMAA&usg=AOvVaw057hjA-BB74HQ44SYMuZan.

Theodore J. Huppert, Monica S. Allen, Heval Benav, Anna Devor, Phil Jones, Anders Dale, and David A. Boas, "A multi-compartment vascular model for inferring arteriole dilation and cerebral meta-

(56) References Cited

OTHER PUBLICATIONS bolic chnages during functional activation", J Cereb Blood Flow Metal. Jun. 2007 ; 26(6): 1262-1279, doi:10.1038/sj.jcbfm.9600435.

Karel Tyml, Donald Anderson, Darcy Lidington, and Hanif M. Ladak, "A new method for assessing arteriolar diameter and hemodynamic resistance using image analysis of vessel lumen", Am J Physiol Heart Circ Physiol 284: H1721-H1728, 2003.

Richard E. Klabunde, PhD "Cardiovascular Physiology Concepts: Systematic Vascular Resistance", Revised Nov. 30, 2014, online: http://cvphysiology.com/Blood%20Pressure/BP021.htm.

Philippe Reymond, Fabrice Merenda, Fabienne Perren, Daniel Rüfenacht and Nikos Stergiopulos, "Validation of a one-dimensional model of the systemic arterial tree", Am J Physiol Heart Circ. Physiol 297:H208-H222, 2009. First published May 3, 2009.

\* cited by examiner

OBTAINING CARDIOVASCULAR PARAMETERS USING ARTERIOLES RELATED TRANSIENT TIME

CROSS-REFERENCE TO RELATED APPLICATION

This application claims the benefit according to 35 U.S.C. 119(e) of a U.S. provisional patent application Ser. No. 61/936,806, filed on Feb. 6, 2014, the disclosure of which is incorporated herein in its entirety by reference.

FIELD AND BACKGROUND OF THE INVENTION

The present invention, in some embodiments thereof, relates to a system, method and apparatus for measuring vascular parameters and, more particularly, but not exclusively, to a system, method and apparatus for monitoring changes in the equivalent inner diameter of small branching arteries and arterioles.

Many medical conditions are characterized by changes or abnormalities and size and shape of arterioles. Vasoconstriction and vasodilation are reversible changes in the diameters of arterioles. Vasoconstriction and vasodilation also play a role in regulating blood pressure, and in diseases characterized by abnormal regulation of blood pressure (hypertension and hypotension), general and peripheral blood flow impedance of subject, systemic vascular resistance (SVR). Other diseases are characterized by chronicle changes in the diameters and cross sections of arterioles, including diabetes and atherosclerosis.

Generally, arterioles are too small to image, using such imaging methods as ultrasound, MRI, and x-rays, including CT scans.

Other techniques for examining the circulatory system are known, for example. sphygmomanometry provides data on systolic and diastolic blood pressure, and pulse oximetry provides data on blood oxygen levels. Arterial line and central venous line sensors provide data on blood pressure and blood flow rate inside large blood vessels.

Josep Sola, Stefano F. Rimoldi, and Yves Allemann, "Ambulatory Monitoring of the Cardiovascular System: the role of Pulse Wave Velocity," in *New Developments in Biomedical Engineering, Chapter* 21, p. 391-422, provides a review of techniques for measuring pulse wave velocity, primarily in large arteries over large distances, for example from the heart to the extremities.

WO2007/097702 discusses a method for the generation, detection and evaluation of a photoplethysmographic (PPG) signal to monitor blood characteristics, in which the light source(s) are spaced at particular distances from photodetector(s). U.S. Pat. Nos. 6,123,719, 5,891,022, US2009/0306487 and EP1297784 discuss photoplethysmographic measurement systems that have at least two light emitters, each emitting light at different wavelengths and a photodiode for detecting the intensity of light reflected from a patient's tissue such as blood, finger, etc.

US2010/0331708 describes methods for monitoring cardiovascular conditions, i.e., hyperblood flow related circulation, vasodilation, vasoconstriction, or central-to-peripheral arterial pressure decoupling conditions. These methods involve measuring a central signal proportional to or a function of the subject's heart activity and a peripheral signal proportional to or a function of a signal related to central signal. Then calculating a time or phase differences between features in the central and peripheral signals representing the same heart event. The cardiovascular condition is indicated if the time or phase difference is greater or lower than a threshold value over a specific period of time, or if there is a significant statistical change in the times over the specific time period. These methods can alert a user that a subject is experiencing some cardiovascular conditions, which can enable a clinician to appropriately provide treatment to the subject.

Said application provides methods, mostly suggesting estimation of common vasoconstriction or vasodilation level, by measurement between physiologically "central", heart-related point and one of physiologically "peripheral" points of measured subject, actually providing estimations of blood flow impedance change along all branches of blood vessel tree, included between said two points. Additional background art includes Reuven Gladshtein, "Indications of cross-section of small branched blood vessels" WO 2012110955 A1, Minnan Xu, "Local Measurement of the Pulse Wave Velocity Using Doppler Ultrasound," M. S. thesis, Dept. of Electrical Engineering and Computer Science, M.I.T., May 24, 2002; A. C. Fowler and M. J. McGuinness, "A Delay Recruitment Model of the Cardiovascular Control System," submitted to Journal of Mathematical Biology, June 2004, revised December 2004; John Allen, "Photoplethysmography and its application in clinical physiological measurement," Physiol. Meas. 28 (2007), R1-R39; H. S. Lim and G. Y. H. Lip, "Arterial stiffness in diabetes and hypertension," Journal of Human Hypertension (2004) 18, 467-468; and Emilie Franceschini, Bruno Lombard, and Joël Piraux, "Ultrasound characterization of red blood cells distribution: a wave scattering simulation study," *Journal of Physics: Conference Series* 269 (2011) 012014.

SUMMARY OF THE INVENTION

An aspect of some embodiments of the invention concerns finding a measure of a blood flow proportional parameter in arteries, and in arterioles that branch off them, and using differences between them to find information about changes in equivalent inner diameter of said arterioles.

Present invention describes a system, indicative or monitoring changes of equivalent inner diameter value over time, the system comprising:

a multiplicity of at least one sensor adapted to obtain signals, correlative to at least one changing over time blood flow related parameter of blood circulation in a subject;

wherein said multiplicity of at least one sensor is adapted to be placed relative to at least one body portion of said measured subject, including branching blood vessels of blood circulation in subject;

wherein said multiplicity of at least one sensor is adapted to obtain at least two signals concurrently, first and second, from said at least one body portion;

wherein said multiplicity of at least one sensor is adapted to obtain said at least two signals from said at least one body portion of subject, wherein an artery-like blood vessels contribute more, relative to an arteriole-like blood vessels, for the first signal than for the second signal;

at least one processor, adapted to use differences between said first and second signals coupled with a heart rate value in order to indicate or monitor changes of equivalent inner diameter value of said arteriole-like blood vessels.

Present invention also describes an apparatus for indication of changes in equivalent inner diameter value of arteriole-like blood vessels or monitoring changes of said equivalent inner diameter value over time, said apparatus comprising:

multiplicity of at least one sensor, including at least one transmitter and at least one receiver, geometrically adapted to sample at least two non-identical volumes of a subject and wherein each of said at least one receiver collects at least one signal, transmitted to measured body portion from said at least one transmitter;

said multiplicity of at least one sensor, adapted to obtain concurrent signals from said at least two non-identical volumes, wherein artery-like blood vessels contribute more, relative to arteriole-like blood vessels, to a signal from a first volume than to a signal from a second volume;

and at least one processor, adapted to indicate changes of equivalent inner diameter of said arteriole-like blood vessels by using differences between said first and second signals coupled with a heart rate value.

Also a new method for estimation of an equivalent inner diameter value of arteriole-like blood vessels or monitoring changes of the equivalent inner diameter value over time in a measured subject, the method for indication of changes in an equivalent inner diameter value of arteriole-like blood vessels, the method comprising:

a) obtaining a first signal, correlative to at least one changing over time blood flow related parameter of blood circulation in artery-like blood vessels and in arteriole-like blood vessels, belonging to a same branching tree of blood circulation;

b) concurrently obtaining a second signal, correlative to at least one changing over time blood flow related parameter of blood circulation in artery-like blood vessels and in arteriole-like blood vessels, belong to the same said branching tree of blood circulation, where said artery-like blood vessels contributing more, relative to said arteriole-like blood vessels, for the said first signal, than for the second signal;

c) obtaining an approximately concurrent heart rate value;

d) obtaining a time differences or phase differences between said the first signal and the second signal; and e) using said time differences or phase differences, coupled with said heart rate value, to indicate changes in an equivalent inner diameter value for the arterioles.

Present invention describes a new system for indication of at least one vascular or cardiovascular condition or monitoring the same, said system comprising at least one processor, configured to process plurality of image, movie or scanned data from at least one body portion, including branching blood vessels, wherein said at least one processor is adapted to indicate from said plurality of images, movie or scanned data:

changes in at least one parameter, correlative to at least one changing in time blood flow related process from at least one artery-like blood vessel;

concurrent changes in at least one parameter, correlative to at least one changing in time blood flow related process from at least one arteriole-like blood vessel or artery-like blood vessel, branched off from same said at least one artery-like blood vessel;

differences between said first and second measured parameters.

Also described a new method for indication of at least one vascular or cardiovascular condition or monitoring the same, said method comprising:

a) transferring image, movie or scanned data collected from body portion, including branching blood vessels, to at least one processor, configured to process said data;

b) extracting by means of said at least one processor, at least one blood flow related parameter, changing over time, said parameter correlative to at least one blood flow related process occurring in at least one artery-like blood vessel;

c) extracting by means of said at least one processor, at least one blood flow related parameter, changing over time concurrently with said above parameter, said parameter correlative to at least one blood flow related process occurring in at least one arteriole-like blood vessel, branched off directly or indirectly from same said at least one artery-like blood vessel;

d) finding differences between said at least first and second measured parameters.

Also described a new apparatus for indication of changes in equivalent inner diameter value of arteriole-like blood vessels or monitoring changes of said equivalent inner diameter value over time, said apparatus comprising:

plurality of sensors, adapted to obtain at least two signals of a subject, wherein at least one of said at least two signals is from peripheral part of blood circulation of subject body;

each of said plurality of sensors, adapted to obtain concurrent signals, proportional to or indicative to heart activity of subject;

and at least one processor, adapted to indicate changes, related to peripheral vasculature by using time differences or phase differences between said at least two signals, coupled with a heart rate value.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 6 B illustrate a final phase of heart beat wave propagation in small arteries, like arterioles, according to an exemplary embodiment of the invention;

FIG. 10 B illustrates three-element Windkessel-type model of arteriole.

FIG. 10 C illustrates three-element Windkessel-type models of arteriole and capillary drain.

FIG. 10 D illustrates Three-element Windkessel-type models of arteriole with capillary drain and precapillary sphincter correction.

DESCRIPTION OF PRINCIPLES AND SPECIFIC EMBODIMENTS OF THE INVENTION

Figure 1:
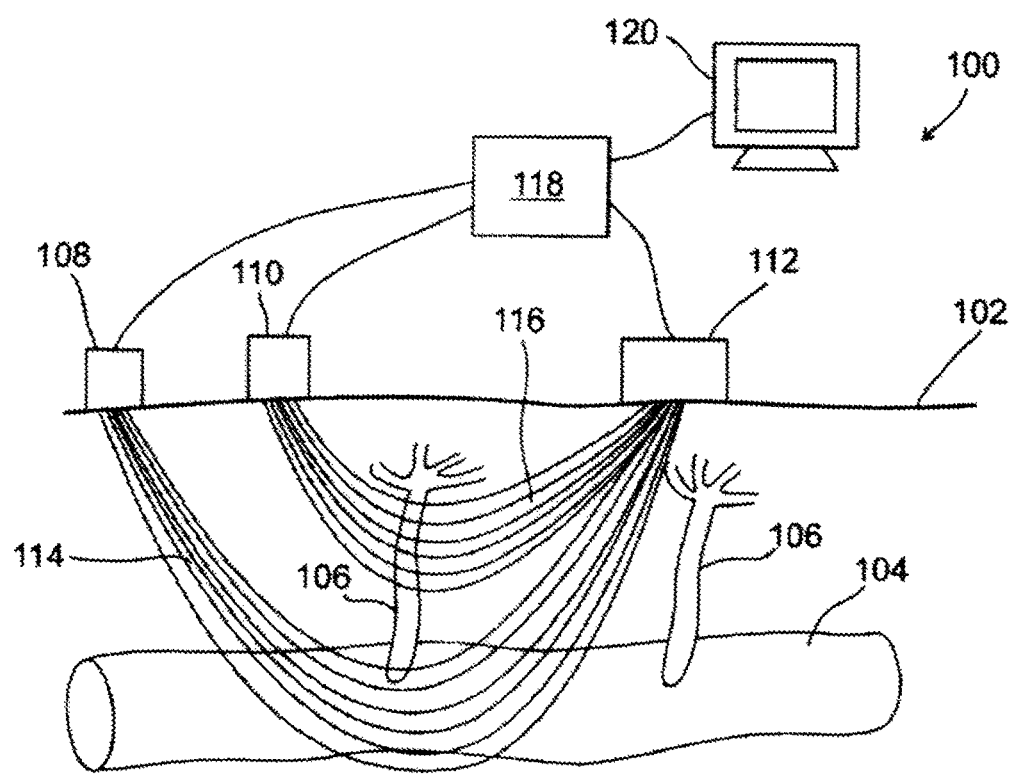
FIG. 1 is a schematic drawing of an optical sensor system being used on a surface of a subject's body to measure blood volume or a related parameter as a function of time in small arteries, and in arterioles branching off from said arteries, according to an exemplary embodiment of the invention.

The present invention, in some embodiments and principles described thereof, relates to a system, method and apparatus for measuring vascular parameters and, more particularly, but not exclusively, to a system, method and apparatus for estimating equivalent inner diameter and for monitoring changes in the equivalent inner diameter of branching arteries and arterioles.

In order to monitor parameters mentioned above in the "Field and Background of the Invention" section, as well as different types of shock, which are characterized also by vasoconstriction or vasodilatation of arterioles at peripheral regions of the body, and in order to monitor their progression, it would be desirable to have a convenient and inexpensive way to continuously monitor the equivalent inner diameter, and changes in the equivalent inner diameter, of arterioles and similar small blood vessels, but no satisfactory technology for that purpose exists at present.

In principle, one could estimate the diameter of arterioles, by combining an optical Doppler measurement of blood flow rate, a photoplethysmography (PPG) sensor to measure blood volume, and an accurate measurement of diastolic pressure inside the blood vessels being examined. But it is difficult to obtain accurate measurements of diastolic pressure in small blood vessels with only external sensors, and besides, optical Doppler measurements of blood flow rate may not be practical for continuous monitoring.

An aspect of some embodiments of the invention relates to finding an estimation of changes in equivalent inner diameter value of small arteries, like arterioles. Two sets of measurements are made, of a physiological parameter that indicates a pressure wave in blood flow of the larger arteries and smaller arteries, like arterioles, the larger blood vessels, like arteries, contribute more, relative to the smaller blood vessels, like arterioles, for the first signal than for the second signal.

Thus said arterioles have higher blood flow impedance, then said branching larger arteries; this difference of impedance causes to time shift (phase shift) in propagation of pulsatile blood flow from said arteries to branched arterioles. It is necessary to keep in mind that physical nature of said time shift is similar to time delay, described in patent applications like US2010/0331708. For example, in US 2010/0331708 time delay is a composite value, consisting from time of blood pressure wave propagation along relatively long blood vessels (central signal) with relatively large diameter and low flow impedance (aorta, big arteries and so on) and characteristic time shift, caused by passing by said blood pressure wave through circulatory branches with sufficiently smaller diameters and lower stiffness (most types of arterioles).

Aorta and arteries have characteristic diameter from 10 mm and more (Aorta) to about 0.4 mm (small arteries) and relatively low ability to change their diameter due to changes of arterial muscle tone. Arterioles have ability to change diameter commonly from 15 to 70 micrometers depends on type, which predefines changes of their flow impedance in very wide range—relatively to flow impedance of previous branching arteries.

It is easy to understand, that significant impedance differences are mainly predefined by naturally existing difference in equivalent inner diameter for said larger arteries and branched from them smaller arterioles (equivalent inner diameter of arterioles are much smaller, difference in equivalent inner diameter is localized at small space of branching) taken into account with much lower stiffness of arterioles, enable them to discover high volume capability, compared to larger branching arteries with significantly higher stiffness.

From other side, discussed here-before prevailing high flow impedance of arterioles, is being connected in serial to said much lower impedance of previous larger arteries in common artery tree of body, make possible to conclude about dominant role of arteriole's impedance on all impedances of larger arteries as different components of common impedance for blood circulation. (See [4], [17] etc.) Thus it makes less important, which relatively big arteries of branching artery tree were selected to measure said time shift relatively to peripheral relatively small arteriole-like arteries. Also changes of common blood flow impedance are mainly defined by changes of impedance of same said arterioles—due to their vasoconstriction or vasodilation, because their ability to change their diameter is much higher that same ability of larger arteries.

Also such factors like number of branches or variation of branching angles in any specific arteriole-like vessel are less significant for complex measurements and analysis of common (averaged) impedance value because influence of these factors to circulation in any tissue region of size, applicable to Photoplethysmographic measurements, is much smaller than same said impedance value and may be neglected.

These facts are well-known in common physiology and physics of circulation and, for example, may be found from [4, 17-19 etc].

Following explanation is for short illustration of ability for skilled in the art to measure signals from mainly region of smaller arteries and mainly region of arterioles, belong to same artery tree of blood circulation. For mammal blood circulation in tissues we may see the following objects of measurement: arteries, arterioles, capillary system, venules and veins.

For example, the green light (~530 nm) enables to analyze blood peripheral perfusion mainly from capillary system and arterioles, characterizing by relatively high blood flow impedance, and characteristic to the tissue layer, close to skin surface. These blood vessels are much less influenced by blood volume changes caused by body movement and bring us information about changes in Peripheral Blood perfusion, cause by arteriole's activities.

Opposite to relatively short visible light wavelengths, using of NIR (Near Infra-Red) light radiation enables measurement and monitoring of physiologic parameters from more deep layers of physiologic tissue.

For example, two transmitters of optical radiation—of green light 530 nm and IR light 940 nm are placed relatively to measured region of tissue by way, enabling to optical receiver measurement of two non-identical physiologic layers of tissue, one—closer to skin surface from green light source and another region—deeper than the first one—from IR radiation source.

The relatively upper measured region includes the capillary system and a part of arterioles and venules. The relatively deeper region, measured by IR light, is mainly represented by small arteries, including relatively much less blood volumes of arterioles, venules and capillary.

NIR is in use to analyze physiologic signals of blood flow, modulated by Heart Rate, Breath processes, Body Movement and so on. And all this because longer wavelengths of light, penetrating biologic tissue deeper, enabling to monitor blood flow processes, associated with relatively larger and deeper blood vessels displaced in inner regions of biologic tissue, such as arteries of various type.

Achieving layers with different depths of measured tissue may be described by other way—using different distances between transmitter and detector of light.

Light energy propagation between emitter and detector within highly scattering matter is deterministic and can be split into a series of smaller "canoe" shaped envelops within which certain fraction of light energy propagates through the matter. The shape of this profile is a function of the source-detector separation, the absorption coefficient, and the reduced scattering coefficient within the tissue. Increases in both tissue scattering and absorption act to reduce the amplitude of the detected signal and reduce measurable the penetration depth.

This approach to signal sampling is an opposite of same approach that regularly is realized, for example, in oxygen saturation measurement.

Usually oxygen saturation measurement needs for sampling of same tissue volume in order to obtain numerical correlations of oxy- and deoxyhemoglobin concentrations with oxygen saturation in blood. Really, said concentrations, being defined through their proportion to amplitudes of heart rate wave, are measured at optical wavelengths, specific to oxy- and deoxyhemoglobin absorption, may be used in same formula of "ratio-of ratios", when being measured from nearly same portion of blood vessels. Systems, methods and devices, described in this invention, in opposite to described here before, use non-identical measured volumes of tissues with branching blood vessel or vessels in order to obtain any of blood flow correlative data types from blood vessels of different size contents.

Thus by measuring a time difference between signals from larger blood vessels, like arteries (excluding arterioles), and smaller blood vessels, similar to arterioles by their physiologic properties, which are related to same measured physiologic region, it is possible to measure difference of local blood flow impedance between said small arteries and arterioles, i.e. to estimate changes in the equivalent inner diameter of said arterioles.

In case the signal from larger blood vessels is measured geometrically relatively far from such a signal from smaller, arteriole-like blood vessels, said measured time difference may be evaluated by several ways as following:

Additional sensor, adapted to obtain arterial signal, may be placed close to sensor, measuring a signal from local small arteries. In this case time difference, measured between arterial signal of "far" sensor and arterial signal of "close" sensor may be used to correct additional time value, measured between "far" arterial signal sensor and sensor of signal from arteriole-like blood vessels. Said measured time difference, actually, is a well-known transit time of pulse wave propagation (PWTT) between said "far" and "close" sensors of signals from larger arteries.

Another way of said time correction may be done by computation, basing on known distance between said "far" and "close" sensors of signals from larger arteries and well-known average values of pulse wave propagation velocity in relatively large arteries (9-12 m/sec, depends on region). Such estimation may be less accurate for computation of the equivalent inner diameter of measured arterioles, but still effective to monitor and track changes of said diameter.

Thus by such a measurement we may separate a PWTT component of said measured time difference from transient time component, including information about changes of diameter in arteriole-like vessels.

It may be also effective in order to define more correctly the role of blood viscosity in monitored vascular condition of patient, for example, to correlate changes of viscosity value with changes of PWTT component, separated from arteriole's transient time etc.

Here after we propose physical explanation, described by two of possible physical models, which illustrates ability to indicate characteristic diameter of arterioles and its changes by use of measured time difference between blood flow wave, propagating in said arterioles and larger arteries, locally branching to said arterioles.

Figure 10A:
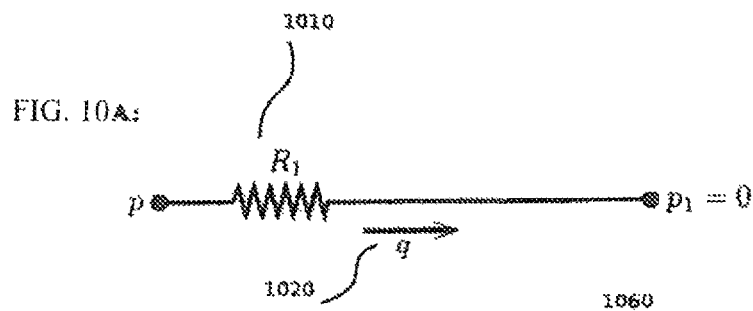
FIG. 10 A illustrates one-element Windkessel-type model of arteriole.
Figure 10B:
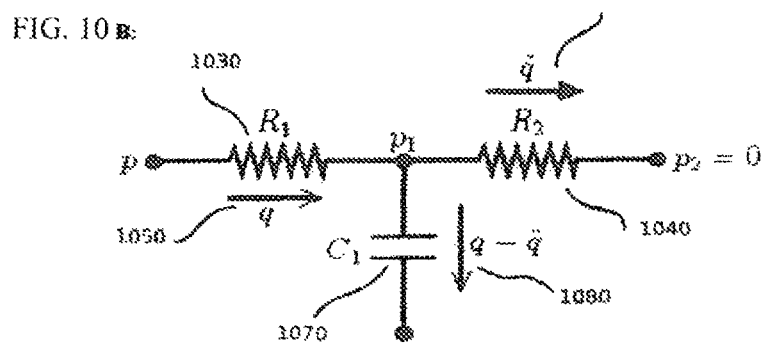
Figure 10C:
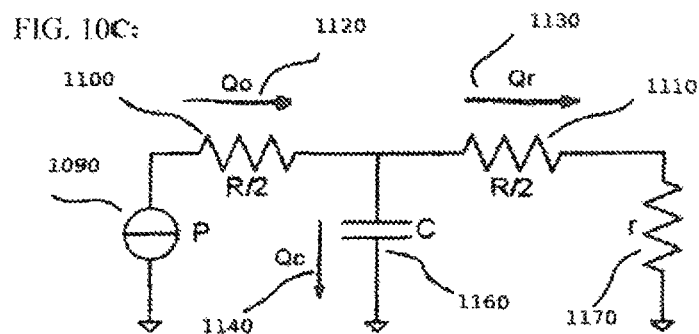

Assuming that the vessel is rigid and the flow is laminar, we may assume that in arteries with a radius smaller than 0.2 cm pressure is proportional to flow [5]. The circuit representing such a vessel (FIG. 10A) would simply contain a resistance 1010 and no other elements. In other words, effects due to inertia and elasticity may be ignored. Since smallest arteries are typically not rigid (although there are exceptions), but do provide resistance, it will be unnecessary to add a capacitor to the model to account for elasticity. However, as shown by Keener and Sneyd [6] it is possible to incorporate elasticity using the two-element Windkessel model; that is, by adding a capacitor 1070 to the circuit shown in (FIG. 10B). It should be noted that the derivation by Keener and Sneyd is somewhat artificial; it includes neither viscosity nor inertia [5]. Thus achieving estimation, basing on Windkessel model with 3 elements, which is widely in use [9,10], analyze small blood vessels with high capability, applied to arteriole-like blood vessel with capillary drain 1170, with the necessary changes having been made (FIG. 10C).

Here we have to keep in mind, that all analytical estimations here-after are only to explain one of possible ways to use value of time or phase shift between signals from larger blood vessels, like small arteries (excluding arterioles), and smaller blood vessels, similar to arterioles by their physiologic properties, localized both at same measured region, but physiologically displaced differently along said region, and measured by skilled in the art in order to achieve correlative estimation to their characteristic equivalent inner diameter value and/or changes of said equivalent inner diameter value.

Thus current models are not described as an exact physical model of blood pressure wave propagation in arteriole and may be modified by skilled in the art mutatis mutandis to achieve physically more exact results without any limitation to general ideas of the patent (For example—[15,16]).

Voltage, current, charge, resistance and capacitance in the electronic circuit are respectively equivalent to blood pressure, blood flow, volume, resistance and compliance in the cardiovascular system. Ground potential of blood pressure (reference for voltage measurements) is assumed to be zero as usual.

Following this analogy to electrical model on FIG. 10C, it is possible to write linear equations of flow Q and pressure P balance for arteriole.

Said model means assumption that blood flow, entering internal space of analyzed arteriole, passes through a half of its viscous resistance before being accumulated in arteriole's capacitance, i.e. before arteriole increases its internal diameter due to its elasticity.

Further process outlines "discharging" of said capacity to capillary drain—through second half of arteriole's resistance.

Voltage, current, charge, resistance and capacitance in the electronic circuit are respectively equivalent to blood pressure, blood flow, volume, resistance and compliance in the cardiovascular system. Ground potential (reference for voltage measurements) is assumed to be zero as usual.

Analysis of the model is regular for skilled in the art and is being made as usual, Windkessel model, combined according to Kirchhoff's Lows, may be written as following $$Q_o = Q_c + Q_r \quad (1)$$

$$P = \frac{Q_c R}{2} + \frac{Q_c - Q_r}{jwC} \quad (2)$$

$$\frac{Q_r - Q_c}{jwC} + Q_r\left(\frac{R}{2} - r\right) = 0 \quad (3)$$

Here R—viscous resistance of arteriole to blood flow, depended on radius of arteriole:

$$R = 8*\eta*L/(\pi*R_a^2)^2, \quad (4)$$

where $R_a$—radius of arteriole, $\eta$—blood viscosity and L—length of arteriole.

C (1160)—capability parameter of arteriole, primarily defined by mechanical elasticity of its walls, depended on radius of arteriole:

$$C = 4*Kart*\pi*R_a^3*L, \quad (5)$$

where $R_a$—radius of arteriole, Kart—capacity coefficient for arteriole and L—length of arteriole.

r (1170)—viscous resistance to blood flow of capillary, being branched off from said arteriole, $$r = 8*\eta*l/(\pi*r_o^4), \text{ depended on radius of arteriole:} \quad (6)$$

where $\eta$—blood viscosity, $r_0$—initial radius of branched capillary and l—length of said capillary.

$Q_o$ (1120)—income blood flow to arteriole, $Q_c$ (1140)—component of blood flow, participating in both first half of arteriole's resistance and capacitance, $Q_r$ (1130)—blood flow through capillary, being branched off from said arteriole.

$f_{hr}$—heart rate, where C and R are parameters, strongly depended on diameter of arteriole.

In modern art there are several ways to estimate viscous resistance R of arteriole to blood flow through arteriole's diameter (Equation 4), for example, by [7] or [8].

In same manner and from similar to [7] or [8] sources viscous resistance r to blood flow in branched capillary and capability parameter C of arteriole may be estimated (Equation 5).

Equations 1-3 are usually used to achieve transfer function or complex impedance of described arteriole system.

After elementary manipulations we get $$P = Q_r \frac{R}{2}\left(\frac{R}{2} - r\right) jwC + \frac{R}{2} Q_r + Q_r\left(\frac{R}{2} - r\right)$$

And finally bring $Q_r$ out of the brackets:

$$P = Q_r \left[\frac{R}{2}\left(\frac{R}{2} - r\right) jwC + R - r\right],$$

where P—is a blood pressure at the entrance of arteriole and $Q_r$ is a drain of arteriole blood flow. Thus arteriole's flow impedance relatively to $Q_r$ is:

$$Z_a = \frac{R}{2}\left(\frac{R}{2} - r\right) jwC + R - r$$

Solving real and imaginary components of arteriole's impedance $Z_a$ relatively to R and C and taking into account that time shift tends to zero at big values of arteriole's diameter, we may determine phase shift $\Theta$, being produced by complex parts of said impedance. Time shift value of arteriole's blood flow may be represented as:

$$\tau = \frac{\Theta}{w} \quad (7)$$

where w—radial frequency of pressure wave: $w = 2\pi f_{hr}$.

Figure 11:
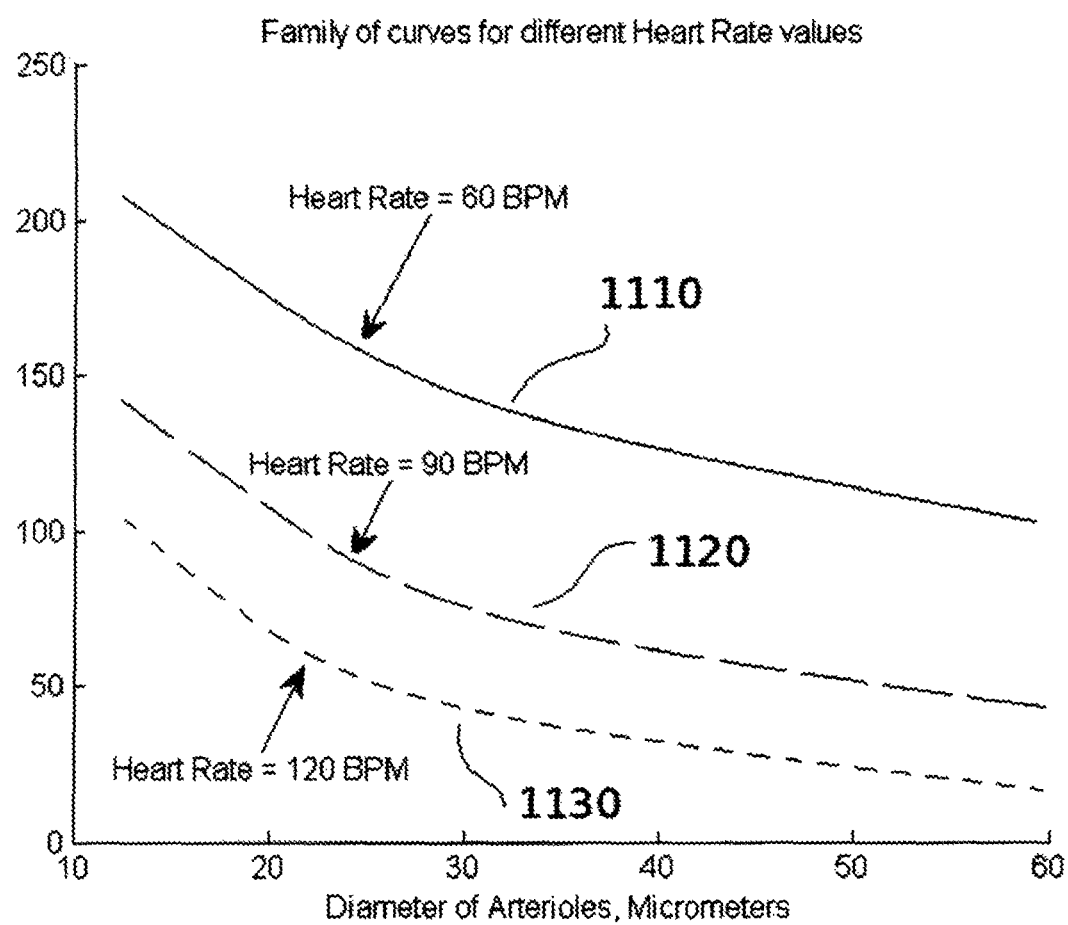
FIG. 11 is an example of results by modeling of arteriole with model, illustrated in FIG. 100.

On FIG. 11 we can see family of curves, where each one is representing dependence of said time shift $\tau$ on diameter of arteriole for different values of heart rate.

On FIG. 11 it is shown that time shift increases, when value of arteriole's diameter have decreased. Also we have to emphasize about very important fact that time shift tends to increase, when heart rate gets slower, even at same values of arteriole's diameter.

It also describes very understandable rule of frequency depended systems functioning: value of heart rate influences significantly to blood flow impedance value and its behavior. Unfortunately absence of this factor in method descriptions and data processing algorithms is characteristic for many applications in prior art, where possible ways for measurement and/or indication of peripheral blood flow impedance or vasoconstriction level is described.

Mentioned in FIG. 100 model has predefined assumptions and some of them may be changed by involving additional facts about physiology of arterioles and capillary, branched off from them, into the model.

Figure 12:
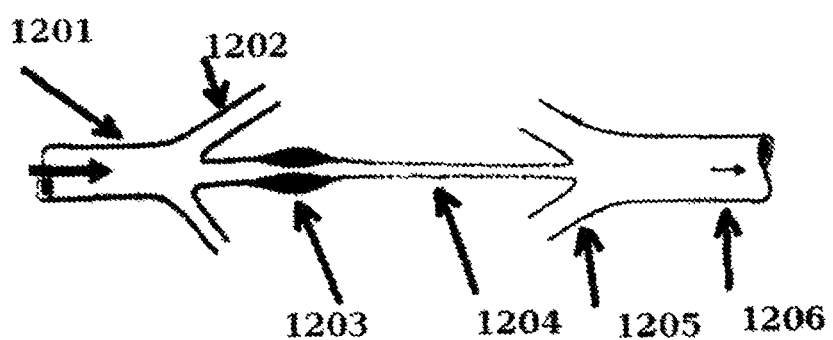
FIG. 12 is a drawing, illustrating function of precapillary sphincter, coupled to arteriole.

As it is possible to see from FIG. 12, at the point where each true capillary 1204 originates from a metarteriole like 1202, a smooth muscle fiber 1203 usually encircles the capillary. This is called the precapillary sphincter. This sphincter can open and close the entrance to the capillary. A precapillary sphincter encircles each capillary branch at the point where it branches from the arteriole. Contraction of the precapillary sphincter can close the arteriole like 1202 off to blood flow. One of functions of precapillary sphincter is by changes of its muscle tone to smooth oscillations of blood pressure at the entrance of branched capillary from small artery 1201 through aerterioles like 1202, when blood flow passes from arteriole to said capillary, by equivalent rC-cuircuit, including capacitance of precapillary sphincter and viscous resistance of branched capillary.

Figure 10D:
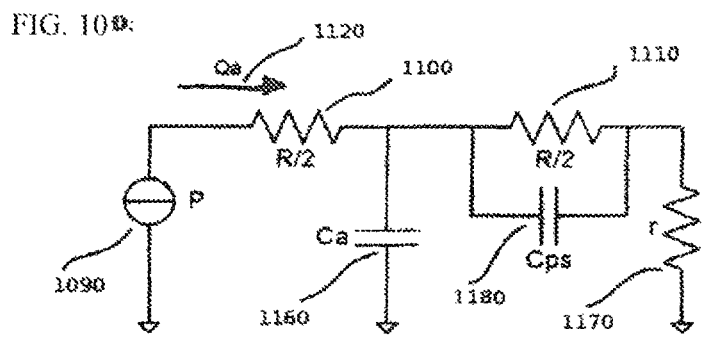

Thus one of possible model interpretations for function of precapillary sphincter, proposed as a final compartment of complex arteriole structure, may be interpreted as capacitive impedance, coupled in parallel to second part of arteriole resistance—before capillary resistance (FIG. 10D).

Impedance of arteriole, describing by model, shown at FIG. 10D, may be written as following:

$$Z_a = \frac{R}{2} + \left(C_a \| (C_{ps} \| \left(\frac{R}{2}\right) + r)\right), \quad (8)$$

Where $C_a$ (1160)—equivalent fluid capacitance of arteriole and $C_{ps}$ (1180)—equivalent fluid capacitance of precapillary sphincter.

Sign $\|$ means parallel connection of equivalent system components in analyzed model.

After transformation of the impedance (5) to its complex form and its evaluation in same manner like in previous model, any skilled in the art may get phase shift and time shift dependence on different values of arteriole's diameter for different rates of heart beats.

Parameters, adapted to averaged physiological parameters of analyzed physiological components of described model, bring same manner of time or phase shift dependence from diameter of arteriole, but here it is realized through hyperbolic-like form of curves.

Figure 13:
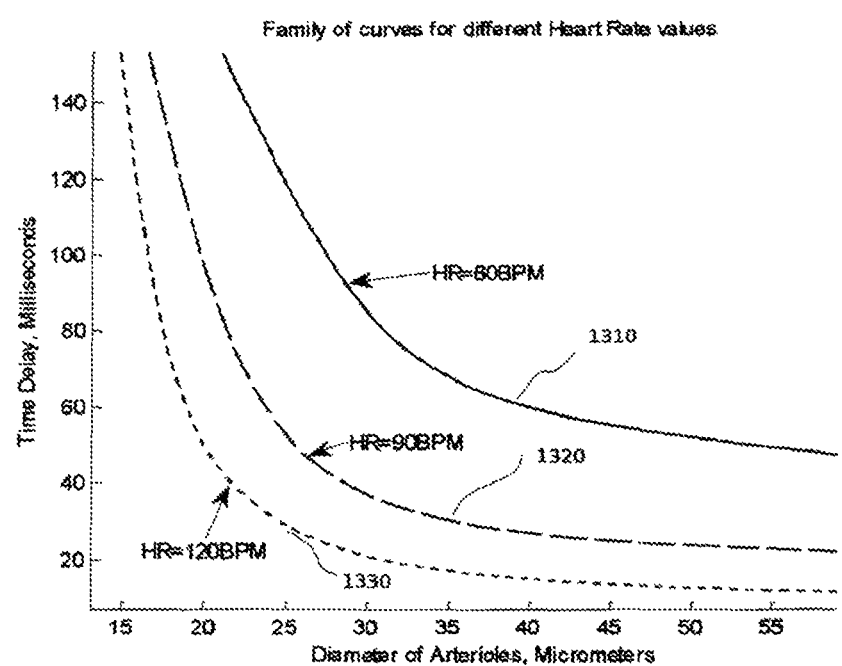
FIG. 13 is an example of results by modeling of arteriole with model, illustrated in FIG. 10D.

An example of calculated results is shown at FIG. 13.

At said figure, like at FIG. 11, specifically time shift was selected to demonstrate abilities of the model, because our working prototype estimates equivalent inner diameter of arterioles by calculation of time shift between signals from arterioles and larger arteries.

Ability to estimate equivalent inner diameter of arterioles enables to determine Systemic Vascular Resistance of measured subject.

Systemic vascular resistance (SVR) refers to the resistance to blood flow offered by all of the systemic vasculature, excluding the pulmonary vasculature. This is sometimes referred as total peripheral resistance (TPR). SVR is therefore determined by factors that influence vascular resistance in individual vascular beds. Mechanisms that cause vasoconstriction increase SVR, and those mechanisms that cause vasodilation decrease SVR. Although SVR is primarily determined by changes in blood vessel diameters, changes in blood viscosity also affect SVR. [13]

According to explained here before we may conclude, that SVR may be mainly defined and/or monitored by monitoring changes of diameter in blood vessels, which diameter is able to sufficient changes. There are mostly arterioles and some other types of small arteries.

So, being able to monitor diameter changes of arteriole-like blood vessels, we enable also to estimate and monitor SVR.

Said US2010/0331708 describes methods involve measuring a central signal proportional to or a function of the subject's heart activity and a peripheral signal proportional to or a function of a signal related to central signal. Then calculating a time difference between features in the central and peripheral signals representing the same heart event.

We have to emphasize about very important fact that time shift tends to increase, when heart rate gets slower, even at same values of arteriole's diameter.

It also describes very understandable rule of frequency depended systems functioning: value of heart rate influences significantly to blood flow impedance value and its behavior. Unfortunately absence of this factor in method descriptions and data processing algorithms is characteristic for many applications in prior art, where possible ways for measurement and/or indication of peripheral blood flow impedance or vasoconstriction level is described.

Our method differs from invented in said patent by including heart rate value, measured concurrently, in process of data collection and processing. According to described in this application, a combination of heart rate values and concurrently measured time or phase differences between signals from larger and smaller arteries, being processed by way, described here, may provide an appropriate indication about said cardiovascular and vascular conditions of subject.

At the same time said large blood vessels with their relatively much lower flow resistance and relatively insufficient ability to change their diameter (i.e. to change their resistance to blood flow), influent SVR much less, than common plurality of said smaller blood vessels in peripheral parts of systemic circulation, thus in some cases may be excluded from SVR measurements.

Without ability to monitor changes in blood vessel diameters SVR may not be monitored directly, but can be calculated if cardiac output (CO), mean arterial pressure (MAP), and central venous pressure (CVP) are known.

$$SVR=(MAP-CVP) \div CO \qquad (9)$$

Because CVP is normally near 0 mmHg, the calculation is sometimes simplified to:

$$SVR=MAP \div CO \qquad (10)$$

It is very important to note that SVR can be calculated from MAP and CO, but it is not determined by either of these variables. A more accurate way to view this relationship is that at a given CO, if the MAP is very high, it is because SVR is high. Mathematically, SVR here is the dependent variable in the above equations; however, physiologically, SVR and CO are normally the independent variables and MAP is the dependent variable.

From other side, the systemic vascular resistance is the resistance to blood flow throughout the circulatory system of the body.

It is controlled by three different factors: length of the blood vessel (l), radius of the blood vessel (r), and the viscosity of the blood ($\eta$). The equation that relates these three factors to resistance is known as Poiseuilles' equation:

$$R \approx (\eta \times l)/r^4 \qquad (11)$$

In the past and till today this formula was not in practical use for SVR definition because direct monitoring of equivalent inner diameter of small blood vessels, like arterioles, was impossible.

Really, for nearly same blood viscosity conditions and same common length of blood vessels in subject's body systemic vascular resistance is defined by equivalent inner diameters of small blood vessels and changes of SVR are depended on changes of said diameters, discussed in current invention, Thus we may conclude that measuring of SVR and its changes is now possible through estimation of equivalent inner diameter of arterioles, and, by coupling it with measurements of Mean Arterial Pressure (MAP) enable to define cardiac output of measured subject.

From (10):

$$CO=MAP \div SVR \qquad (12)$$

In same manner it is easy to show, that, by coupling independent measurements of SVR from (9) or (10) and equivalent inner diameter of arterioles, it is possible to monitor changes of blood viscosity. From (11):

$$\eta \approx SVR \times r^4/l, \qquad (13)$$

where l (common length of the blood vessels) is a constant and 2xr—equivalent inner diameter of arterioles. Or, alternatively from (10) and (13):

$$\eta \approx MAP \times r^4/(CO \times l) \qquad (14)$$

An estimation of $\eta$ according to (13) or (14) may be done by use of technology, estimating equivalent inner diameter of arterioles, coupled with any other measuring system, estimating SVR or MAP and CO independently.

Also independent estimating SVR or MAP and CO may be more effective and/or accurate using our invention.

For example, "Nihon Kohden" technology estimates stroke volume (SV) by principle of esCCO, where an inverse correlation between stroke volume (SV) and pulse wave transit time (PWTT) is found. [20] "Nihon Kohden" describes PWTT as following:

"PWTT as the time measured from the ECG R-wave peak to the rise point of $SpO_2$ pulse wave. PWTT consists of the following three time components.
1. PEP: Pre-ejection period including the electromechanical delay at the start of systole and isometric contraction time, with the R wave of ECG serving as the starting point.
2. $T_1$: The time it takes for pulse wave to travel from the aorta through the elastic arteries to the muscular arteries
3. $T_2$: The time it takes for pulse wave to travel from the muscular artery to the further distal peripheral site of $SpO_2$ measurement."

"Nihon Kohden" further writes:

"PEP is affected by cardiac contractility, preload and afterload, and is reduced as stroke volume (SV) increases. In peripheral vessels with small diameter, propagation velocity of pulse wave is reduced because the impact of viscosity becomes dominant. When there is no change in vascular diameter, $T_2$ is less affected by viscosity. However, viscosity can have a dominant influence on $T_2$ when vascular diameter is smaller, so $T_2$ is affected by vascular diameter. As vascular diameter determines vascular resistance, we assume that $T_2$ is affected by vascular resistance. Considering the relationship between SV and $T_2$, $T_2$ is reduced as SV is increased due to vasodilatation with increased vascular diameter." Although well-understood general conclusion regarding dependence manner between SV and T2, authors were not correct regarding main factors of influence on $T_2$, relating it to viscosity factor only. It is right that decreasing diameter of smallest arteries increases role of viscosity when vascular resistance is determined.

But vasoconstriction of smallest arteries, like arterioles, causes also changing (increasing) of arterioles transient time, a local transient effect of blood wave propagation from significantly lower impedance of muscular arteries to significantly larger impedance of small arterioles, described in our invention here above.

Taking this transient time into account may define $T_2$ transit phase of PWTT more correctly, thus balancing relative weights of blood viscosity and changes of diameter by small arteries in influencing said $T_2$.

Due to unitary nature of human physiology, characteristic diameter of healthy arterioles, their stiffness, width of walls and other mechanical parameters in any predefined region of each healthy humane with normal cardiovascular conditions belongs to limited range of characteristic values (for example, value of characteristic diameter of arterioles may be about 35 microns in some peripheral body regions), so estimations here above are reasonable for each healthy human. Changes in some physiological conditions of measured subject, like heart rate, have been taken into account also, when such estimation is done, as was explained therebefore.

Summarizing an issue of arterioles diameter measurement, we have to emphasize, that invented here systems, methods and devices, indirectly measuring changes in characteristic diameter of arterioles or value of said diameter, may be proved and/or calibrated by use any of existing absolute methods of measurements, like in [11].

It may be done, for example, by same way, like in pulse-oximetry, where computed from measured signals values of oxygen saturation are corrected to more exact values by means of initially prepared "Correction Table". Such a "Correction Table" may be achieved, for example, by comparison of calculated equivalent inner diameter values of arterioles for preselected measurement conditions, like heart rate, to actually measured by one of direct measurement methods, like in [11].

The measurements of the pressure wave may be, for example, measurements of blood volume in tissue, for example optical measurements, ultrasound measurements, or electrical impedance measurements. The measurements may also be, for example, measurements of blood flow rate, for example laser Doppler measurements. The measurements may be measurements of oxygen or carbon dioxide levels in blood or tissue, for example optical measurements. The two sets of measurements may distinguish larger blood vessels from the smaller blood vessels that branch off them, by penetrating to different characteristic distances beneath the surface of the body. Smaller blood vessels that branch off from larger blood vessels typically extend closer to the surface than the larger blood vessels they branch off from. For example, if optical measurements are used, then larger blood vessels can be measured using a wavelength of light that penetrates further into the tissue, such as near infrared, while smaller blood vessels can be measured using a wavelength of light that does not penetrate as far, for example green light. Both near infrared light, and green light, are suitable for measuring blood volume, because they are both preferentially absorbed by blood over other tissue, and other wavelengths can also be used for this reason. Wavelengths can also be used even if they are not preferentially absorbed by blood, if they provide an estimation of the pressure wave in a different way, for example by providing a measure of blood oxygen level or carbon dioxide level. Similarly, if ultrasound measurements are used to measure blood volume, then lower frequencies, which penetrate further into tissue, may be used to measure the larger blood vessels, while higher frequencies are used to measure the smaller blood vessels. In addition, for either optical or ultrasound measurements, the large blood vessels can be measured using a source (light source or ultrasound transducer) that is further away, on the surface of the body, from the detector, while the smaller blood vessels, closer to the surface of the body, can be measured using a source that is closer, along the surface of the body, to the detector, so that the signal is dominated by light or ultrasound that has not penetrated very far beneath the surface. Similarly, for electrical impedance measurements, electrodes can be placed further from each other on the surface of the body, to measure larger blood vessels, which are deeper in the body, and closer to each on the surface of the body, to measure smaller blood vessels, which are closer to the surface of the body.

In some embodiments of the invention, the first set of measurements is made using a sensor placed relative to (aimed to) blood vessels close to a surface, large enough to be visible to the naked eye, or through an endoscope, and the second set of measurements is made using a sensor placed in a nearby area of the surface where there is no large blood vessel, visible to the naked eye or through an endoscope, near the surface, so the measurements will be dominated by smaller blood vessels that branch off the larger blood vessel. This method may be particularly useful for measurements made of the surfaces of internal organs, external parts of eye and so on, for example by endoscope or during surgery, for which relatively large blood vessels are likely to be visible on the surface, for diagnostics of eye sclera or blood vessels related investigations in small animals. It is reasonable to use CCD-like sensors in such a cases.

Again, the measurements can comprise using optical, ultrasound or electrical impedance measurements to measure blood volume, or laser Doppler measurements to measure blood flow rate. Optionally, the measurements are also made on larger blood vessels, to provide a reference case, where the viscous drag is relatively small, for comparison.

Either of these methods can be used to assess various medical conditions. Vasoconstriction, which is a reversible decrease in blood vessel diameter, specifically for arterioles, can be an indication of shock, dehydration or blood pressure changes. Pathological conditions such as diabetes, or atherosclerosis, can cause long term irreversible narrowing of small blood vessels, or changing of equivalent inner diameter value, and can be diagnosed or monitored using these methods. For these pathological conditions, narrowing of the blood vessels may be associated with a change in time shift between larger and smaller blood vessels, or a change in phase shift between larger and smaller blood vessels, if the blood vessel walls also become stiffer due to the pathological condition, but measuring these quantities can still be used to distinguish damaged small blood vessels, from healthy ones.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Referring now to the drawings, FIG. 1 illustrates an optical sensor system 100, for example a photoplethysmography (PPG) system, used to measure blood volume, or a related parameter such as blood or tissue oxygen level or carbon dioxide level, as a function of time in a region of a surface 102 of a subject's body, according to an exemplary embodiment of the invention. Optionally, surface 102 is the subject's skin, and sensor system 100 is non-invasive. Alternatively, system 100 can be used on an internal surface of the subject's body, for example on a surface of an internal organ during surgery, in an endoscopic procedure or during long term internal monitoring or monitoring of internal organ, for example in the nasal passage, in the gastrointestinal tract, in the ear, or in the urethra. Blood vessels like 104, at some distance beneath surface 102, has smaller blood vessels 106 branching off it. When blood vessels have smaller blood vessels branching off it, the smaller blood vessels often come closer to the surface than the larger blood vessels, especially when the surface is the skin. For example, blood vessels like 104 are a relatively small artery, about 7 mm beneath the surface, and vessels 106 are arterioles, which come closer to the surface than vessels like 104, for example within 2 mm, 3 mm or 4 mm of the surface.

Light sources 108 and 110, being placed relatively to measured tissue region, aimed into surface 102 and optionally in contact with surface 102, illuminate the blood vessels, and light scattered from the blood vessels is detected by detector 112. Light source 108 produces light of a relatively long wavelength, for example near infrared light, that can penetrate deeply enough into body tissue to reach the depth of blood vessels like 104, while light source 110 produces light of a shorter wavelength, for example green light, which largely does not penetrate the tissue as far as blood vessels like 104, but mainly illuminates smaller blood vessels 106, that are closer to the surface. In this way, detector 112 can generate a first signal to which blood vessels like 104 make a substantial contribution, and a second signal to which blood vessels like 104 make a smaller contribution, if any, and smaller blood vessels 106 make a relatively larger contribution.

For example, the light from light source 108 penetrates to a characteristic fall-off distance of 3 mm, or 5 mm, or 10 mm, or more than 10 mm, or less than 3 mm, or an intermediate distance. A characteristic fall-off distance in tissue for light from light source 110 is smaller than the characteristic fall-off distance for light from light source 108, for example by a factor of at least 1.3, or at least 1.5, or at least 2, or at least 3, or at least 5. For example, the light from light source 110 penetrates to a characteristic fall-off distance of 1 mm, or 2 mm, or 3 mm, or 5 mm into the tissue, or a greater, smaller, or intermediate distance. Optionally, one or both of light sources 108 and 110 is an LED, or a laser diode. In some embodiments of the invention, light sources 108 and 110 comprise a single light source, which produces two different wavelength bands of light, a longer wavelength band of light which penetrates more deeply into the tissue, and a shorter wavelength band of light which penetrates less deeply. In some embodiments of the invention, the light source or separate light sources produce three or more wavelength bands of light, which penetrate into the tissue respectively a shorter distance, one or more different intermediate distances, and a longer distance. Using three or more wavelength bands may provide more accurate results for time differences as a function of penetration distance, because there is some redundancy. Additional wavelength bands may also be used to measure different parameters, for example both blood volume, and blood oxygenation level, which may provide more accurate results.

In addition to, or instead of, using a wavelength range for light source 108 that penetrates tissue more deeply than a wavelength range used for light source 110, the light detected from light source 108 will come from a deeper layer of tissue than the light detected from light source 110, if light source 108 is located further away from its detector than light source 110 is. Light detector 112 is optionally positioned relatively to measured region of tissue on surface 102, close enough to light source 108 that it can detect a substantial amount of light from light source 108 that scatters from tissue at the depth of blood vessels like 104, but not so close to light source 108 that light from light source 108 scattering from a shallower depth in the tissue, for example at the depth of blood vessels 106, overwhelms the light scattered from tissue at the depth of blood vessels like 104. For example, light detector 112 is located at a distance from light source 108 equal to 0.5 times a characteristic fall-off distance in tissue of the light from light source 108, or equal to the characteristic fall-off distance, or equal to 2 times the characteristic fall off distance, or 3 times the characteristic fall off distance, or equal to 3 mm, or 5 mm, or 10 mm, or 20 mm, or 30 mm, or equal to a smaller, greater, or immediate distance. Optionally, light detector 112 is also used to detect light from light source 110 that scatters from tissue at a shallower depth, or a separate light detector is used for that purpose. Light detector 112, or a separate light detector if one is used, is located close enough to light source 110 so that it detects a substantial amount of light from light source 110 that scatters from tissue at the depth of blood vessels 106, but not so close that light scattered from a shallower depths overwhelms the light scattered from tissue at the depth of blood vessels 106. For example, light detector 112, or a separate light detector used for light source 110, is located relatively to light source 110 at distance equal to 0.5 times a characteristic fall-off distance in tissue of the light from light source 110, or equal to the characteristic fall-off distance, or equal to 2 times the characteristic fall off distance, or 3 times the characteristic fall off distance, or equal to 0.5 mm, or 1 mm, or 2 mm, or 5 mm, or 10 mm, or equal to 1 times, 1.5 times, 2 times, 3 times, 5 times or 10 times the distance between light source 108 and light detector 112, or equal to a smaller, greater, or immediate distance. If there are three or more light sources producing light of different wavelengths which penetrate to other distances into the tissue, then the light sources producing the more deeply penetrating light are optionally located further from the detector, or their individual detector, than the light sources producing the less deeply penetrating light.

When system 100 operates, light source 108 produces light 114, directed into the tissue beneath surface 102, which scatters relatively more from blood vessels like 104, and relatively less from smaller blood vessels 106, and is detected by detector 112, while light source 110 produces light 116, directed into the tissue beneath surface 102, which scatters relatively more from smaller blood vessels 106, and relatively less from blood vessels like 104, and is detected by light detector 112, or by a different light detector as noted above. It should be understood that "relatively more" and "relatively less," mean that the ratio of light scattered from blood vessels like 104 to light scattered from blood vessels 106 is greater for light produced by light source 108 and detected by light detector 112, than it is for light produced by light source 110 and detected by light detector 112. Optionally, the ratio is 1.2 times as great, or 1.5 times as great, or 2 times as great, or 5 times and great, or 10 times as great, or a smaller, greater, or intermediate number of times as great. Optionally, more of the light produced by light source 108 and detected by light detector 112 is scattered by blood vessels like 104 than by blood vessels 106, for example 1.2 times as much, or 1.5 times as much, or 2 times as much, or 5 times as much, or 10 times as much, or a smaller, greater, or intermediate number of times as much. Optionally, more of the light produced by light source 110 and detected by light detector 112 is scattered by blood vessels 106 than by blood vessels like 104, for example 1.2 times as much, or 1.5 times as much, or 2 times as much, or 5 times as much, or 10 times as much, or a smaller, greater, or intermediate number of times as much.

Optionally, light sources 108 and 110 placed relatively to measured tissue region such way, that illuminate the tissue beneath surface 102 simultaneously, and light detector 112 distinguishes between light from light source 108 and light from light source 110 by using filters, or using two detectors that are each sensitive to wavelengths from a different one of the light sources. Alternatively, light coming from light source 108 is distinguished from light coming from light source 110 by multiplexing, i.e. the light sources are alternately turned on and off, with only one of the light sources on at a given time. However, if such multiplexing is used, it may be advantageous to do it rapidly enough, for example with on and off times of several milliseconds or less, so that a time shift between signals from the two light sources, that is only a few tens of milliseconds, can be accurately measured, as will be explained below.

The light from light source 108 detected by light detector 112, scattered relatively more from blood vessels like 104 and less from smaller blood vessels 106 than the light from light source 110 is, provides a measure of the volume of blood or a related parameter in blood vessels like 104, in the vicinity of the light sources and detector, as a function of time. The light from light source 110 detected by light source 112, scattered relatively more from blood vessels 106, and less from blood vessel 104, provides a measure of the volume of blood or a related parameter in blood vessels 106, in the vicinity of the light sources and detector, as a function of time. Two signals produced by detector 112, one of light produced by light source 108 and one of light produced by light source 110, are sent to a controller 118, for example a computer or dedicated circuitry. Controller 118 compares the two signals, and, as will be described below in the description of FIG. 5, uses the signals to obtain information about the equivalent inner diameter of blood vessels 106, or about a change in the equivalent inner diameter of blood vessels 106, or a difference in the equivalent inner diameter in different parts of the body. As it was shown in theoretical part of this description, proper estimation of equivalent inner diameter needs of heart rate value taken into account. Said heart rate value has to be obtained at same time, when detector 112 produces said signals. In current embodiment the heart rate value may be calculated from at least one of measured said signals, or, alternatively, may be obtained from any other sensor or any other device.

Alternatively or additionally, other parameters of the blood vessels may be found, for example the mean arterial pressure may be found if there is other information about heart stroke parameter.

Even if the signals from light produced by light source 108 and light produced by light source 110 are not dominated respectively by scattering from blood vessels like 104 and scattering from blood vessels 106, in some embodiments of the invention due to different relative contributions to the signals from scattering from blood vessels like 104 and scattering from blood vessels 106, controller 118 is able to separate the contribution from blood vessels like 104 from the contribution from blood vessels 106, and to create two output signals that, subject to noise and other limitations of the data, represent only or primarily scattering from blood vessels like 104 and blood vessels 106 respectively. Optionally, controller 118 uses those two output signals, instead of or in addition to the two signals of light produced by light source 108 and light produced by light source 110, to find the information about the equivalent inner diameter or change or difference in equivalent inner diameter of blood vessels 106.

Optionally, controller 118 is connected to an I/O device 120, such as a display screen, a printer, a touch screen, a keyboard, and/or a mouse, that allows users to see the results of calculations done by controller 118. Optionally, controller 118 also controls and/or detects when light sources 108 and 110 are turned on. Optionally, a user can use the input features of I/O device 120 to turn system 100 on, and/or to control parameters used by controller 118 in analyzing the signals from light detector 112, optionally using a graphic user interface. Controller 118, I/O device 120, and the light sources and detector need not be physically located in the same room, but may be remote from each other, connected by communications links. For example, I/O device may be a cell phone or a Bluetooth device, used to monitor a patient remotely. I/O device 120 may also be located next to the patient, or even on a device worn by the patient, such as a bracelet with a display screen, so medical personnel can easily read off data from it when examining the patient.

Figure 4:
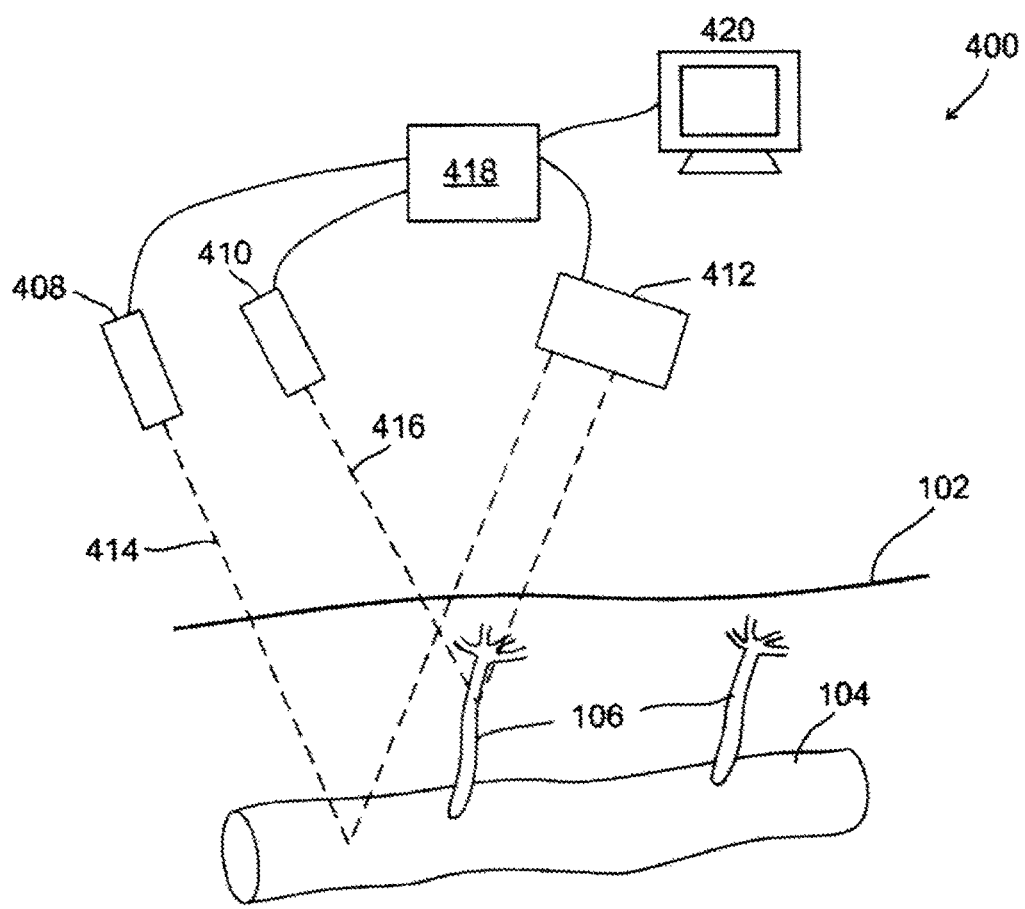
FIG. 4 is a schematic drawing of a laser Doppler system being used to measure blood flow rate as a function of time in a larger arteries, and in smaller arteries, like arterioles branching off from said arteries, according to an exemplary embodiment of the invention.

It should be understood that elements with a function attributed to controller 118, for example A/D converters, or CPUs, may also be located in detector 112, and this is true also for the system shown in FIG. 4, and the detectors or receivers, and controllers, in the system. Alternatively, such elements may be considered part of controller 118, even if they are housed in a same physical unit as detector 112. In general, controller 118, and the other controller in FIG. 4, need not be a single physical unit, but are optionally distributed in a plurality of different places or combined with different pieces of hardware.

It should also be understood that more than one system such as system 100, or elements of more than one such system, may be used on a same subject. For example, different types of sensors, such as those in FIG. 1 or 4, may be used together, with different controllers, or with a single controller that performs the control functions for all of the sensors.

Light scattered from tissue provides a measure of the blood volume in the scattering region, if the light is of a wavelength or band of wavelengths that is absorbed and/or scattered at a rate different from the rest of the tissue, and this is true of the light produced by light sources 108 and 110. For example, the light produced by light source 110 is optionally in an absorption band of oxyhemoglobin, if system 100 is designed to be used for arteries, or deoxyhemoglobin if system 100 is designed to be used for veins. The light produced by light source 108 is optionally in a wavelength range, in the near infrared, that is absorbed by water with an absorption length on the order of 1 cm or a few cm, for example between 0.9 and 1.4 µm, so would be preferentially absorbed by blood, which has a higher percentage of water than the surrounding tissue, but would not be almost completely absorbed before it reaches blood vessels like 104.

In some embodiments of the invention, light sources 108 and 110 use wavelengths that are not preferentially absorbed by blood over other tissue, but that are preferentially absorbed by oxyhemoglobin over deoxyhemoglobin, or vice versa, or that are absorbed by carbon dioxide, for example in the infrared at 2.15 µm or 4.2 µm. Such wavelengths are used by optical pulse oximeters, and by optical capnometers. In this case, the signal produced need not be a measure of blood volume, but may be a measure of oxygen level or carbon dioxide level in the blood, and in tissue. Since oxygen levels and carbon dioxide levels in the blood, and in tissue, may vary periodically over the cardiac cycle and over the breathing cycle, they may be used, as an alternative to blood volume, to find a time differences between the signals, as described in FIG. 5.

In some embodiments of the invention, there are a plurality of different light sources 108 located at different distances from detector 112, and/or a plurality of different light sources 110 located at different distances from detector 112, and/or a plurality of different detectors 112 located at different distances from light sources 108 and 110. The distance between light source 108 and detector 112, and/or the distance between light source 110 and detector 112, can then be optimized, by looking at the signal for each distance between the light sources and the detector, and optionally only using the signals that work best. Optionally, there are also a plurality of light source and detectors pairs at the same separation distance, but located at different places, and the location can be optimized by looking at the signal from each pair, and optionally only using the signal that works best. Some locations may work better than other locations because, for example, the light source and detector are positioned better with respect to blood vessels that are suitable for measuring vasoconstriction, or that are suitable for detecting narrowing of blood vessels due to a pathological condition, such as diabetes, that may only affect blood vessels in some locations.

From description of the embodiment, discussed above, we may see, that it is possible to achieve different separation levels between measured signal from artery-like and arteriole-like blood vessels. In theory, obtaining at least two signals, wherein the first one includes not significantly more from artery-like blood vessels, then the second one, we are able to calculate the difference between them and, according to known anatomy of measured body portion, estimate equivalent inner diameter of arteriole-like blood vessels by appropriate numerical correction.

But much better the situation, where said different separation levels between measured signal from artery-like and arteriole-like blood vessels is sufficient, thus enabling to estimate equivalent inner diameter of arteriole-like blood vessels without significant numerical corrections.

An ideal is the case, wherein we obtain at least two signals from artery-like and arteriole-like blood vessels, being fully or almost fully separated.

Here after an example embodiment of modified pulse-oximeter is described and this is also to example of almost full separation between signaling from artery-like and arteriole-like blood vessels.

We see much reason also to reflect here an additional possibility for estimation of arteriole's equivalent inner diameter, where the analyzed blood vessels are observed visually or may be observed by different optical magnification or optical scanning means. This possibility enables finding different blood flow related processes in each artery-like or arteriole-like blood vessel by digital processing of data, obtained from their imaging or scanning examinations, in separate.

Calculated here time or phase differences are represented in their optimal conditions, thus performing the best correlation to different vascular or cardiovascular conditions in measured subject.

Traditionally there is well developed technique, enables to image retinal blood vessels with resolution and accuracy, good enough to quantitative analysis.

The technique is related to fundus ophthalmoscopy and fundus photography.

Ophthalmoscopy (also called fundoscopy) is a test that allows to see inside the back of the eye (called the fundus) and other structures using a magnifying instrument (ophthalmoscope) and a light source.

Usually it is done as part of an eye exam and may be done as part of a routine physical exam. The fundus contains a lining of nerve cells (the retina), which detects images seen by the clear, outer covering of the eye (cornea). The fundus also contains blood vessels and the optic nerve Compared to ophthalmoscopy, fundus photography generally needs a considerably larger instrument, but has the advantage of availing the image to be examined by a specialist at another location and/or time, as well as providing photo documentation for future reference. Modern fundus photographs generally recreate considerably larger areas of the fundus than what can be seen at any one time with handheld ophthalmoscopes.

Both types of these retinal monitoring techniques enable to observe different sizes of retinal vessels, being recognized there separately one from another. Thus here we may speak about comparison of two separate arterial vessels of different sizes.

As it was described for previous embodiment, in this invention we find from measured blood vessels proportion or correlation blood flow related process, changing over time. It means that instead of one image of retinal blood vessels we have to collect a number of different images in any of data formats (image data)—in order to be able to calculate some parameters, said about changes in measured blood vessels due to blood flow propagation over time.

During its collection or after being collected, said image data has to be transferred to processor unit for further analysis.

Figure 2:
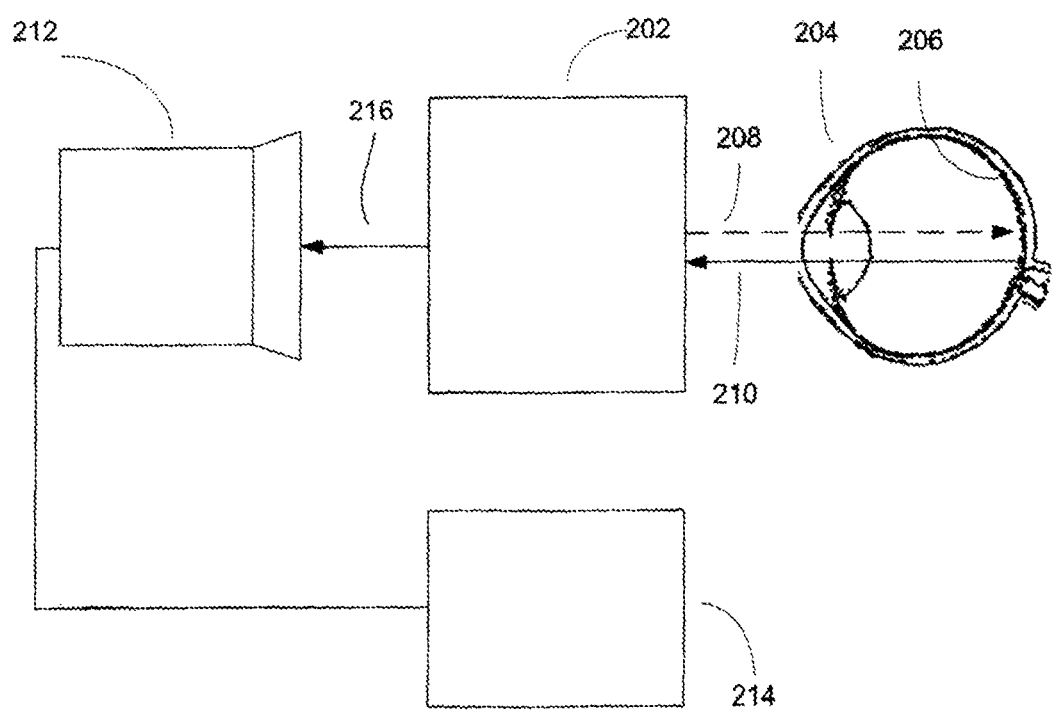
FIG. 2 is a schematic drawing of an ocular fundus imager, according to an exemplary embodiment of the invention.

FIG. 2 illustrates a system of said ocular fundus imager, which may be used for estimating of equivalent inner diameter of retinal arterioles.

The system includes ophthalmoscopic device 202, irradiating light 208 to retinal surface 206 of eye 204. The portion of light 210 comes back to ophthalmoscopic device and, being optically prepared to focused retinal image 216, is collected by image sensor 212, which is able to collect images with proper rate.

Transformed from images by image sensor 212 image data in its digital form is transferred to local or remote processor unit 214 for immediate or further analysis.

As it was done in previous embodiment, estimation of arteriole's equivalent inner diameter in eye's retina is possible by at least partial separation between blood flow related signals from larger retinal arteries and blood flow signals from smaller retinal arteries, like arterioles.

Basic properties of focused image enable to separate between said signals through using object analysis from said image data.

Each branching blood vessel has its unique place in collected image, thus enabling to analyze it separately.

Being identified by image data, said blood vessel may be analyzed by its configuration and brightness parameters and their changes over time in order to estimate their proportion or correlation to at least one of blood flow related processes.

Figure 3A:
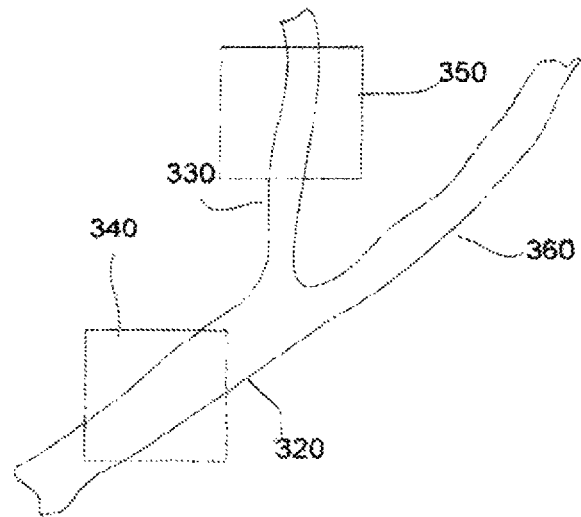
FIG. 3A is a schematic drawing of retinal artery, splitting to two arteries of nearly same diameter.

FIG. 3A illustrates splitting of two smaller retinal arteries 330 and 360 of nearly same diameter from larger retinal artery.320.

When processor 214 performs analyzing of image data, including, for example an image portion with illustrated by FIG. 3A, at least one analysis area may be selected for each blood vessel.

On FIG. 3A is shown analysis area 340 for branching retinal artery 320 and analysis area 360 for branched smaller retinal artery 330.

Blood flow proportional or correlative process from vessel-related portions of said areas may be achieved by separate or combined analysis of their brightness and geometric properties. At least some of these properties tend to vary over time according to blood flow propagation there.

Really, physical parameters of blood flow in said vessels, like changes of blood pressure, blood volume or blood velocity over time, cause to blood vessel with finite stiffness to change its diameter and, sometimes, also its geometrical position in retinal space (vasomotion).

Being illuminated by external light 208, such a vessel varies its reflectance properties that cause to changes in geometric and brightness parameters of collected over time image data.

Taking into account, that larger artery is much rigid, than branched smaller arteries and much more rigid than its brunched arterioles, we may conclude, that diameter changes, caused by blood flow propagation to said artery, will be much less, than for its branched arterioles. Said difference has also to be taken into account for proper use of processor unit 214.

Figure 3B:
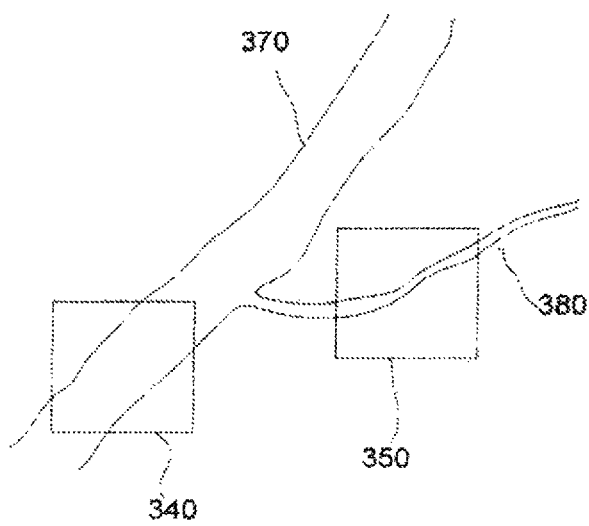
FIG. 3B illustrates splitting of retinal arteriole from retinal artery.

FIG. 3B illustrates splitting of retinal arteriole 380 from larger retinal artery 370, when selected area of analysis 340 for said artery and selected area of analysis 350 for said arteriole may be analyzed by different ways.

Due to sufficient diameter of artery 370 it may be useful to analyze, for example, changes in brightness in margins of its internal area.

For smaller arteriole 380 internal variations of brightness may be insufficient for detailed analysis, but, because of its higher elasticity, changes of its diameter may be recognized much easier that in case of larger and relatively rigid retinal artery 370.

Figure 14:
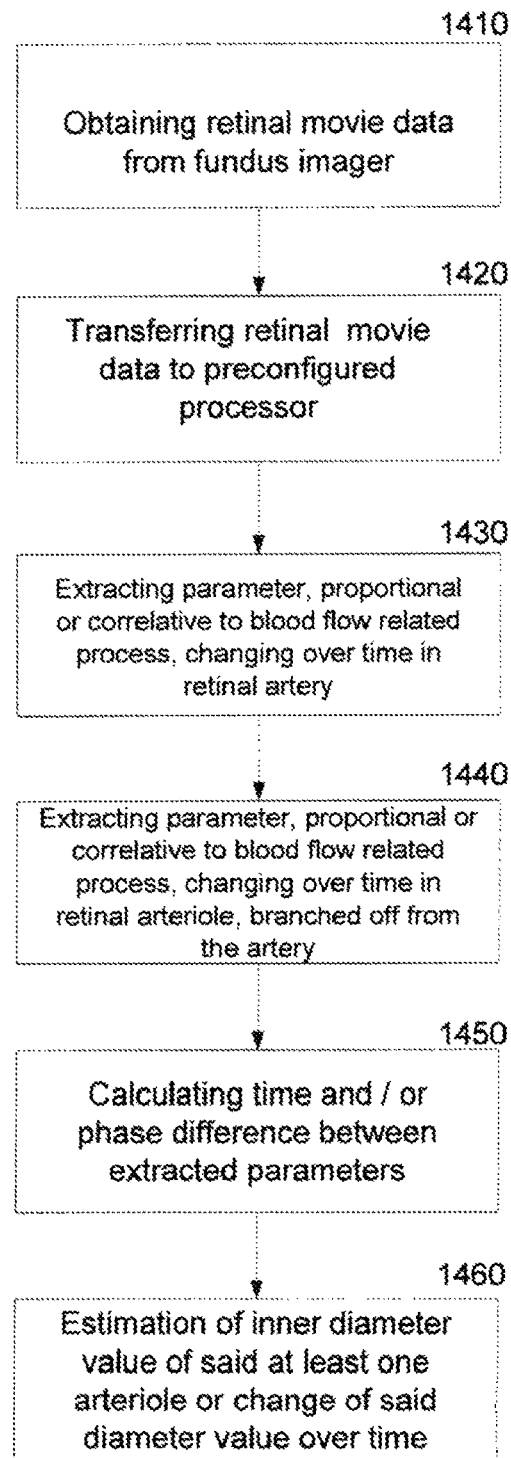
FIG. 14 is a flowchart for an exemplary method of estimation for equivalent inner diameter of retinal arteriole, branched off from retinal artery, and optionally monitoring changes in value of said diameter over time, by calculating from ophthalmoscopy data at least one changing over time parameter of blood flow relative process in said analyzed retinal artery and arteriole according to an exemplary embodiment of the invention.

On FIG. 14 a flowchart illustrates an example for an exemplary method of estimation for equivalent inner diameter of retinal arteriole, branched off from retinal artery, and optionally monitoring changes in value of said diameter over time, by calculating from image data at least one changing over time parameter of blood flow relative process in said analyzed retinal artery and arteriole according to an exemplary embodiment of the invention.

Here the first stage 1410 comprises obtaining of retinal movie data from fundus imager.

Said data at the following step 1420 is being transferred to preconfigured processor for further process. Said processor extracts blood flow proportional parameters, changing over time, from at least one larger retinal artery (1430) and from at least one smaller retinal artery, belongs to same artery tree, like said larger artery (1440). It may be arteriole, branched directly from said larger artery. Also it may be at least one smaller artery, branched from same said larger artery and so on.

Optionally it may be extraction of blood flow proportional parameters, changing over time, from all arteries, branching from said larger artery.

Said processor calculates time or phase shift between said time-dependent parameters, extracted from larger and smaller retinal vessels (1450) in order to estimate, coupling this data with heart rate value, obtained at the time period of image data collection, equivalent inner diameter value of said smaller retinal blood vessels (1460).

Heart rate value, used for estimation of equivalent inner diameter of smaller retinal vessel, may be obtained from analysis of same said blood flow proportional or correlative over time parameter, extracted from said image data, Optionally or alternatively heart rate value may be obtained from independent measurement, performed at a time of collecting same said image data by same ophthalmologic device or by any other device, intended for this measurement.

Following potential ability of retinal image technology also to collect retinal images at relatively high rate, we may illustrate a way of estimation for heart beat wave propagation velocity by means of analysis, described before.

On FIGS. 6 A and B two different phases of heart beat wave propagation from branching retinal artery 620 to smaller retinal arteriole 630 are illustrated.

Figure 6A:
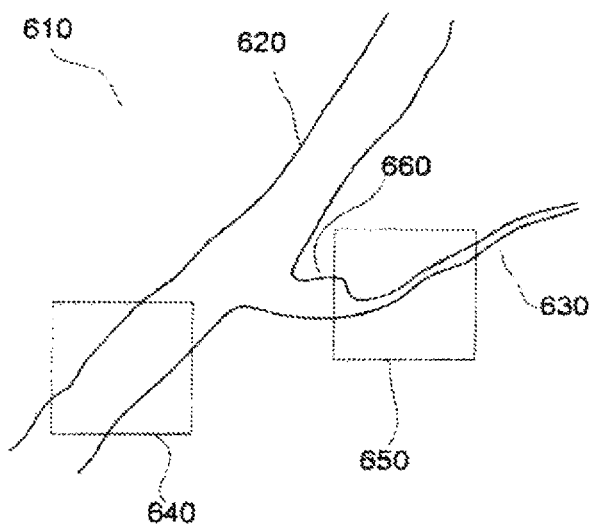
FIG. 6 A illustrate an initial phase of heart beat wave propagation in small arteries, like arterioles, according to an exemplary embodiment of the invention.

On FIG. 6A the frontal part 660 of current heart beat wave widens initially small diameter of said arteriole 630 and this widening may be analyzed in selected area of analysis 650.

Figure 6B:
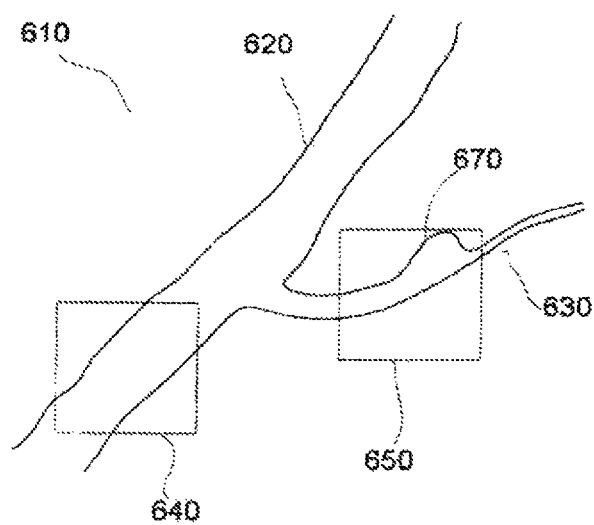

On FIG. 6B, by using appropriate rate of image collecting after some time we may recognize similar widening 670 in other place of selected area of analysis 650, distanced from its initial place on FIG. 6A.

Said measurable distance between positions of said frontal part 660 on FIG. 6A and on FIG. 6B, in couple with known time range between collecting their appropriate image data, enables to calculate heart beat wave propagation velocity in said retinal arteriole.

Figure 15:
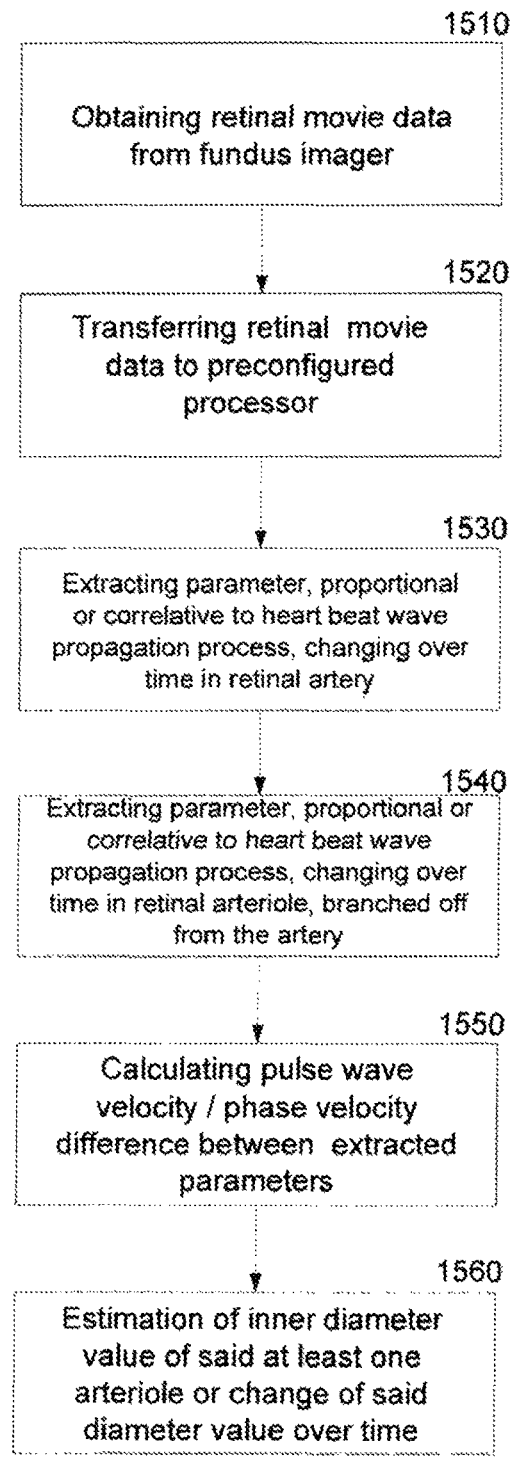
FIG. 15 is a flowchart for an exemplary method of estimation for equivalent inner diameter of retinal arteriole, branched off from retinal artery, and optionally monitoring changes in value of said diameter over time, by calculating from ophthalmoscopy data at least one changing over time parameter of pulse wave propagation relative process in said analyzed retinal artery and arteriole according to an exemplary embodiment of the invention.

On FIG. 15 a flowchart illustrates an example of method for estimation of equivalent inner diameter of retinal arteriole, branched off from retinal artery, and optionally monitoring changes in value of said diameter over time, by calculating from ophthalmoscopy data at least one changing over time parameter of pulse wave propagation relative process in said analyzed retinal artery and arteriole according to an exemplary embodiment of the invention.

Here the first stage 1510 comprises obtaining of retinal movie data from fundus imager.

Said data at the following step 1520 is being transferred to preconfigured processor for further process. Said processor extracts time of pulse wave propagation trough said larger (1530) and smaller (1540) retinal arteries. It may be arteriole, branched directly from said larger artery. Also it may be at least one smaller artery, branched from same said larger artery or any other possible branch.

Optionally this extraction may be performed by analysis of geometrical changes in blood vessel configurations of collected image data or in changes of their brightness.

Said processor estimates equivalent inner diameter value by use of said extracts time of pulse wave propagation trough said larger (1530) and smaller (1540) retinal arteries, in coupling this data with heart rate value, obtained at the time period of image data collection, equivalent inner diameter value of said smaller retinal blood vessels (1560).

Heart rate value, used for estimation of equivalent inner diameter of smaller retinal vessel, may be obtained from analysis of same said blood flow proportional or correlative over time parameter, extracted from said image data, Also here optionally or alternatively heart rate value may be obtained from independent measurement, performed at a time of collecting same said image data by same ophthalmologic device or by any other device, intended for this measurement.

Ophthalmologic fundus imaging is also based on Doppler-based optical scanning (See [13,14] and more).

Doppler fundus imaging in its various implementations enables to reach parameter, proportional to or correlative to velocity of blood in measured arteries and arterioles of retina.

It also may be a parameter for estimation of equivalent inner diameter of retinal arterioles by use of its time or phase differences in scanned retinal arteries and arterioles over time.

It is necessary to remind regarding two widespread diagnostic methods in fundus ophthalmology, where an option for direct measurement of blood velocity is possible without use of Doppler Effect.

In Fluorescentic Fundus Ophthalmology a mixture with fluorescent dye is injected into circulation and enables to observe it flow in retinal imaging without application of external illumination.

By imaging of fluorescent dye components moving in retinal blood vessel tree it is also possible to estimate characteristic velocity of blood in each of imaged blood vessels over time.

Same principle of blood velocity estimation may be applied in case of autofluorescense retinal imaging, where for example, illuminated by specific wavelengths red blood cells (RBC) of blood in retinal blood vessels irradiate their own fluorescent light, which is imaged by ophthalmologic device.

Generally, estimated by methods, illustrated in FIGS. 14 and 15, results may be represented at different numerical and graphical forms, including also retinal mapping in case of said image data processing, applied to one or several sectors of retinal image.

FIG. 4 shows a system 400 that uses laser Doppler measurements to measure a blood flow rate in blood vessels like 104, and in one or more of blood vessels 106. A laser Doppler system 408 scatters one or more laser beams from moving erythrocytes in blood vessels like 104, which are received by a detector 412. A laser Doppler system 410 scatters one or more laser beams from moving erythrocytes in one or more of blood vessels 106, which are received by detector 412, or by a separate detector. Optionally, laser Doppler system 408 uses a wavelength of light that penetrates further into the tissue beneath surface 102, so it can reach blood vessels like 104 while remaining coherent, than the light of laser Doppler system 410, which only has to penetrate as far as blood vessels 106. Alternatively, they use the same wavelength. Detector 412 optionally uses the different wavelengths to distinguish the signals from the two laser Doppler systems. Alternatively, detector 412 uses multiplexing to distinguish the signals.

Detector 412 sends signals from the two laser Doppler systems to a controller 418, which uses the signals to calculate a flow rate of blood in blood vessels like 104, and a flow rate of blood in one or more of blood vessels 106, as a function of time. Optionally, because there may be many blood vessels 106 oriented in many different directions, and it may be difficult to determine the direction of orientation of a particular blood vessels 106 that is being measured, laser Doppler system 410 makes a 2D or 3D measurement of blood vessels 106, so that the flow rate can be found as a function of time, by controller 418, even if the orientation of the vessel is not known. Optionally this is also done by laser Doppler system 408 for blood vessels like 104.

Figure 5:
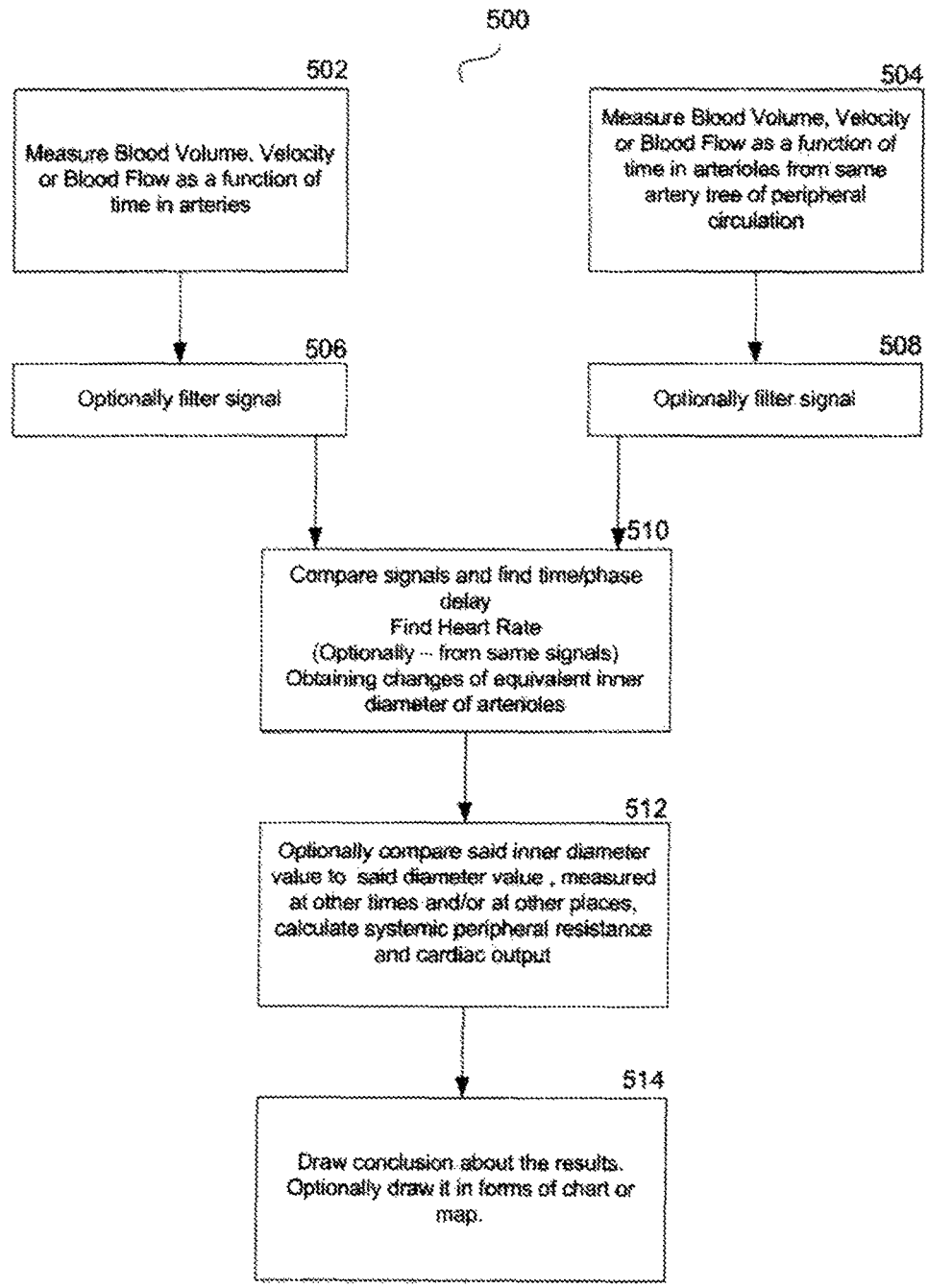
FIG. 5 is a flowchart for a method of finding the equivalent inner diameter of smaller arteries, like arterioles branching off from larger arteries, or changes in the said equivalent inner diameter, for example using the systems shown in FIGS. 1,2 and 4, using a time or phase shift in the pulse wave between said small arteries and the arterioles, according to an exemplary embodiment of the invention.

Because blood flow rate, like blood volume, varies in blood vessels like 104 and 106 over time, depending on the pressure, the signals of blood flow rate, like the signals of blood volume, can be used to measure the pressure wave in blood vessels like 104 and 106, and hence can be used by controller 418 to find information about the equivalent inner diameter, change in equivalent inner diameter or difference in equivalent inner diameter of blood vessels 106, in coupling with obtained at the same time value of heart rate, as will be described below in the description of FIG. 5. In some embodiments of the invention, as noted above, only the signal from blood vessels 106 is needed, and for those embodiments, the flow speed or velocity in blood vessels like 104 need not be measured.

FIG. 5 shows a flowchart 500, for a method of using measurements for one or more larger blood vessels and for smaller blood vessels that branch off the larger vessels, to find information about the equivalent inner diameter of the smaller vessels, and/or about changes in the equivalent inner diameter over time, and/or about differences in the equivalent inner diameter between different parts of the body. The measurements can be any measurement in the larger and smaller blood vessels, as a function of time, that depends on the pressure, and provides an indication of a pressure wave in those blood vessels, for example blood volume, flow rate, or oxygen level or carbon dioxide level in blood or tissue. The term "pressure wave" as used herein includes the variation in blood pressure in arteries due to the cardiac cycle, as well as a variation in blood pressure in veins due to motion of the subject's body, or any other cause of short-term temporal variation of pressure in blood vessels.

At 502, a measurement is made of blood volume or blood flow as a function of time in the smaller blood vessels, and at 504, simultaneously with 502, or with a known time shift, a measurement is made of blood volume or blood flow rate as a function of time in the larger blood vessels, using any of the methods described in FIGS. 1 and 4, for example. At 506, the signal from the smaller vessels is optionally filtered to remove noise, optionally by low-pass filtering, and at 508 the signal from the larger blood vessels is optionally filtered to remove noise, optionally by low-pass filtering. The low-pass filtering removes high frequency noise from the signals, but optionally the filtering is not so strong that the overall shape of the signal on the time scale of the pressure wave is greatly distorted. In particular, the filtering is not so strong as to introduce substantial errors in a time or phase shift calculation between the two signals. For example, frequencies up to 5 times the heart beat frequency, or up to 10 times the heart beat frequencies, are not filtered very much, but higher frequencies are. Optionally, very low frequency components, for example at frequencies below the frequency of the heart beat, are also filtered out, to detrend the data, or the data is detrended in another way. At 510, the two signals are compared, and time or phase differences are found between them, for example by finding a time shift that maximizes their equivalent inner diameter value. The time shift, coupling with heart rate value at the time of measurement, provides information about the diameter of the smaller vessels.

At 512, the equivalent inner diameter valueis optionally compared to an equivalent inner diameter value found at other times or in other parts of the body, optionally in the same way as this time shift. At 514, conclusions are drawn about the equivalent inner diameter of the small blood vessels. These conclusions need not involve absolute measures of the equivalent inner diameter value, but could involve only changes in the equivalent inner diameter over time, possibly only about the direction of change. Additionally or alternatively, the conclusions could involve differences in the equivalent inner diameter, possibly only the sign of the difference, between this part of the body and other parts of the body.

In some embodiments of the invention, conclusions are drawn about the equivalent inner diameter of small blood vessels, based on whether or not the equivalent inner diameter is smaller than a threshold value. For example, the threshold value is between 20 and 50 micrometer and if the equivalent inner diameter exceeds the threshold value, then conclusions are drawn that small blood vessels being measured exhibit vasoconstriction or vasodilation. Optionally, the threshold is specific for a patient, and/or for a particular method of measurement. Optionally, the threshold is determined by earlier testing of that patient, and is stored in a controller, such as controllers 118, or 418 of FIGS. 1 and 4 respectively, that performs the step of drawing conclusions about the equivalent inner diameter of the small blood vessels at 514.

In general, a larger time or phase shift means smaller equivalent inner diameter of the smaller blood vessels, at least if the smaller blood vessel walls are not also becoming more rigid when the diameter gets smaller. That seems to be the case with normal, reversible vasoconstriction in healthy subjects, as indicated by the observations described below under "Examples." That data was obtained by inducing vasoconstriction by cooling part of the body. But vasoconstriction can also be sign of such dangerous medical conditions as shock and dehydration, and the method of flowchart 500 can be used to help diagnose such conditions, as will be described in more detail in the description of FIG. 9. In those cases, vasoconstriction occurs first in peripheral parts of the body, and can work its way closer to the central parts of the body, i.e. closer to the trunk, as the condition gets more severe. Monitoring vasoconstriction in such circumstances can be clinically useful, and it is not necessary to be able to calibrate the equivalent inner diameter to the exact diameter of the smaller blood vessels. It may be enough to observe qualitatively that the small blood vessel equivalent inner diameter is decreasing in time, more severely in peripheral parts of the body.

The method of flowchart 500 can also be used to measure changes in the equivalent inner diameter s of small blood vessels due to causes other than vasoconstriction. For example, pathologies such as diabetes, and atherosclerosis, may cause a narrowing of smaller arteries, and it can be clinically useful to monitor such changes over time, for example over months or years. In general, it may not be known, from first principles, whether progression of diabetes or atherosclerosis would be expected to lead to an increase or decrease in equivalent inner diameter value in smaller arteries, and it may not even be the same for all patients. Even in these circumstances, measuring equivalent inner diameter value repeatedly at different times can be useful, just by showing a change in equivalent inner diameter value, in either direction. Also, particularly in the case of diabetic patients, there may be parts of the body where it is clear, from clinical indications, that small arteries have not yet been affect adversely by the disease, and these parts of the body may provide a reference for comparison, that can be used to evaluate the direction of change in equivalent inner diameter value in smaller arteries in areas that are affected. Further details on using this method to evaluate patients with pathologies such as diabetes, are provided in the description of FIG. 8, below.

Figure 7:
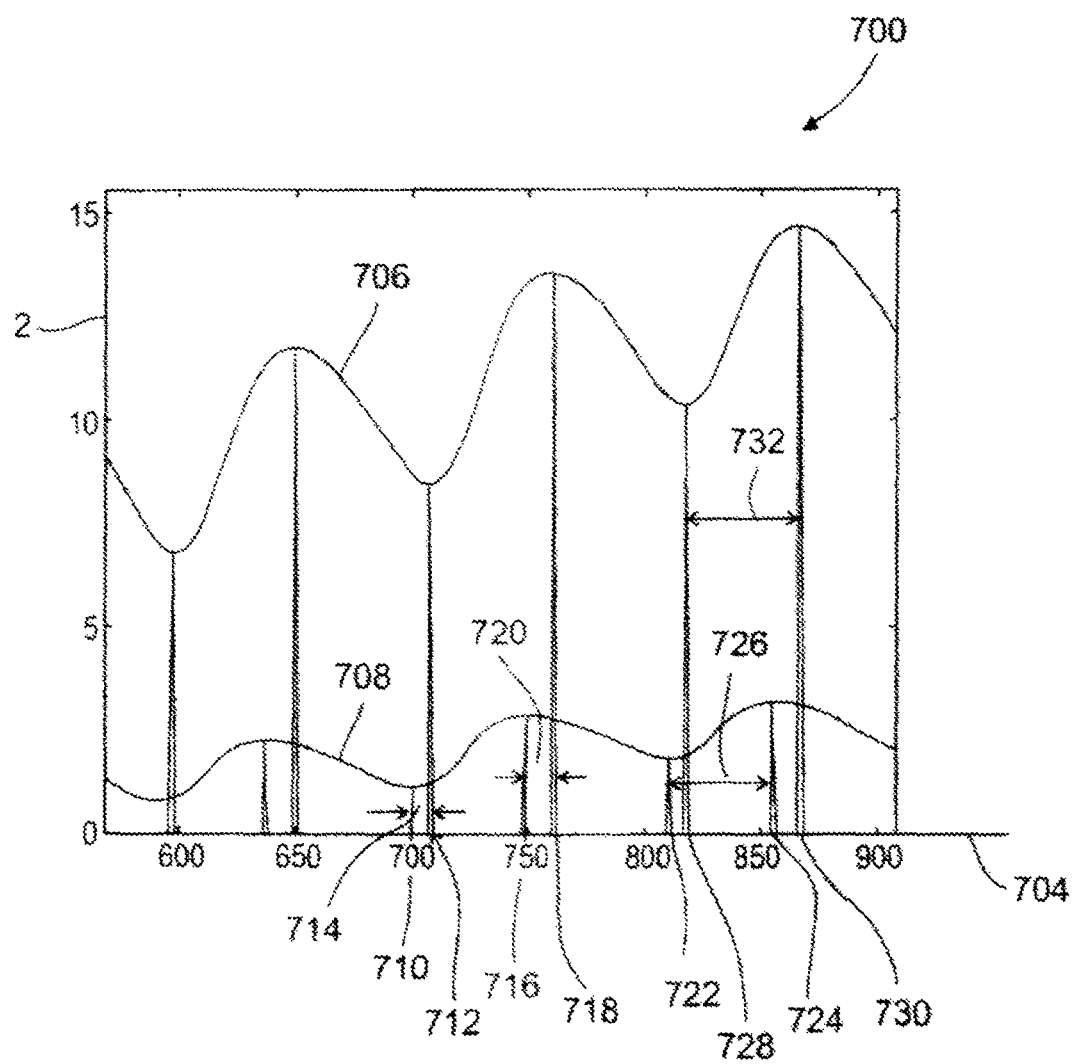
FIG. 7 is a schematic drawing showing a pulse wave as a function of time primarily in a larger arteries, and primarily in smaller arteries, like arterioles, branching off from the said larger arteries, for example using a photoplethysmography system similar to the optical sensor systems shown in FIG. 1 or 4.

FIG. 7 shows a plot 700 of photoplethysmographic (PPG) signals for green and near infrared light, for the same location on the body of a test subject, to illustrate how the time differences may be found from the signals. The signals were obtained with a PPG system similar to system 100 shown in FIG. 1. The amplitude of the signal is plotted on a vertical axis 702, in arbitrary units, and the time is shown on a horizontal axis 704, also in arbitrary units. Curve 706 is the PPG signal using green light, which is sensitive primarily to the blood volume in the arterioles, while curve 708 is the PPG signal using near infrared light, which is sensitive primarily to the blood volume in the artery or arteries that the arterioles are branching off from. The signals have been low-pass filtered to remove noise, but still show the general shape of pressure waves in the artery and the arterioles. The signals have been inverted so that a more positive value of the signal indicates a greater volume of blood, even though a greater volume of blood results in a lower intensity of light scattered from the tissue, since the green light used for signal 706 and the near infrared light used for signal 708 are both absorbed more by blood than the surrounding tissue. Optionally, signals 706 and 708 are de-trended before finding the time differences, to remove drift in the signal from one cardiac period to the next that can distort the shape of the signal, although that was not done with signals 706 and 708 shown in FIG. 7.

To find a time delay between signal 706 and signal 708, a time difference is found for corresponding points on curve 706 and curve 708. For example, minima of the two signals, for the same cardiac cycle, may be used to find the time difference. Time 710 is a minimum of curve 708, and time 712 is the minimum of curve 706 for the same cardiac cycle. A difference 714 between time 712 and time 710 is optionally used as the time shift for these two signals. Alternatively, maxima of the two signals, for the same cardiac cycle, may be used to find the time shift. Time 716 is a maximum of curve 708, and time 718 is a maximum of curve 706 for the same cardiac cycle. A difference 720 between time 718 and time 716 is optionally used as the time shift between these two signals. Although time shift 714 is different from time shift 720, due to the different shape of curves 706 and 708, the time shift may be meaningfully compared at different times, and/or at different parts of the body, if the time shift is defined consistently. Still other procedures for measuring time shift include looking at the time difference of an inflection point, for example the time of greatest rate of rise, or the time of greatest rate of fall, for the two signals, or looking at the time difference between points that are half-way between the local minimum and local maximum in amplitude, or in time, for the two signals. The time difference can also be found by finding a time shift that maximizes a cross-correlation between the two signals. Optionally, the time shift, however it is found, is averaged over multiple cardiac periods, for example to reduce noise.

Optionally, before finding the time difference, the signal is examined to make sure that it is a good signal. For example, if the signal comes from arteries, it is examined to verify that its dominant component is at a reasonable cardiac frequency, optionally between 0.5 and 3 Hz.

Figure 8:
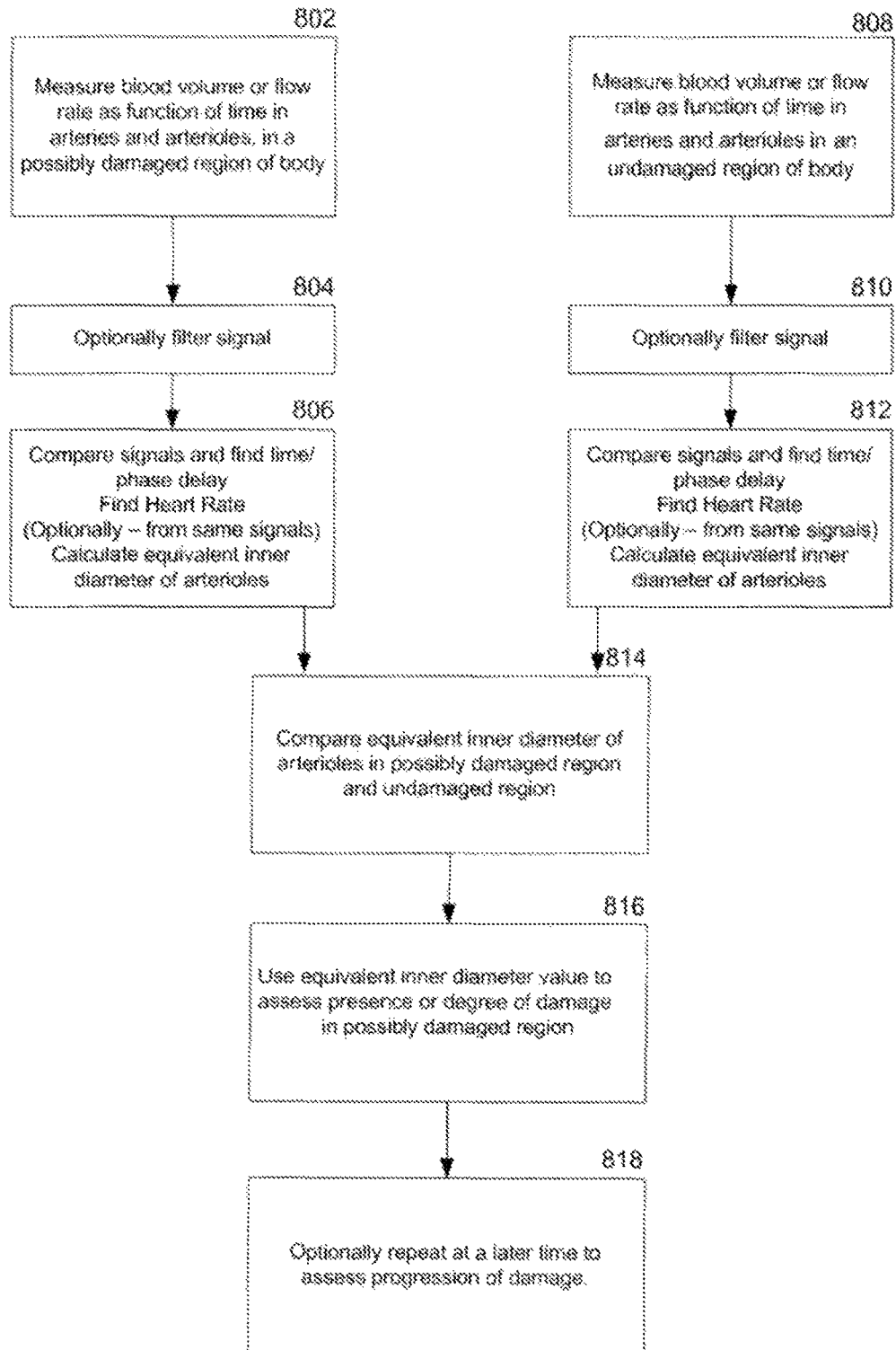
FIG. 8 is a flowchart for an exemplary method of evaluating damage in arterioles that branch off small arteries, in patients with pathological conditions such as diabetes, according to an exemplary embodiment of the invention.

FIG. 8 is a flowchart for a method of assessing or monitoring damage to small blood vessels due a pathological condition such as diabetes, using the method of FIG. 5. At 802, a quantity that serves as an indication of a pressure wave in blood vessels, such as blood volume or blood flow rate, is measured in a larger branching blood vessels and in the smaller blood vessels that belong to same peripheral part of systemic circulation, for example using one of the systems shown in FIGS. 1, 2 and 4, in a part of a body of a patient that is believed to have damage from a disease, such as diabetes, that can damage small blood vessels. Signals from these measurements are optionally low-pass filtered, at 804, and optionally detrended. A time or phase difference between the two signals, for the larger and smaller blood vessels, is found at 806. At 808, measurements are made, similar to the measurements made at 802, but for a part of the body where the small blood vessels are believed to be undamaged, or less damaged, by the pathological condition. The signals from these measurements are optionally filtered at 810, and a time or phase difference between the larger and smaller blood vessels is found at 812, and, being coupled with obtained heart rata value related to said measuring time, fn equivalent inner diameter value may be estimated.

At 814, the equivalent inner diameter values from the region believed to be damaged, and the region believed to be undamaged or less damaged, are compared, and results of the comparison are used, at 816, to assess the presence or degree of damage to small blood vessels, in the region believed to be damaged.

Optionally, if the method is being used to monitor a patient with diabetes, which often effects small blood vessels only in scattered localized regions of tissue without affecting other regions as much or at all, then an array of sets of sensors and detectors, each set similar to those shown in FIG. 1 is used over a large area on a general part of the body, for example the foot, that is likely to be affected in some locations, in order to monitor the whole area at once.

The method of flowchart 800 may be particular suited for assessing damage to small blood vessels due to diabetes (for example, in foot or Retina), since diabetes typically causes such damage to small blood vessels in some parts of the body and not in others, so it is usually possible to find regions, known to be relatively undamaged by diabetes, which can be used as a reference. The method of flowchart 800 may be less suited for assessing damage to small blood vessels due to atherosclerosis, since such damage may be more widespread throughout the body, and it may be difficult to find undamaged areas for comparison, but it may still be possible to use the method of flowchart 800 for assessing damage to small blood vessels due to atherosclerosis.

Figure 9:
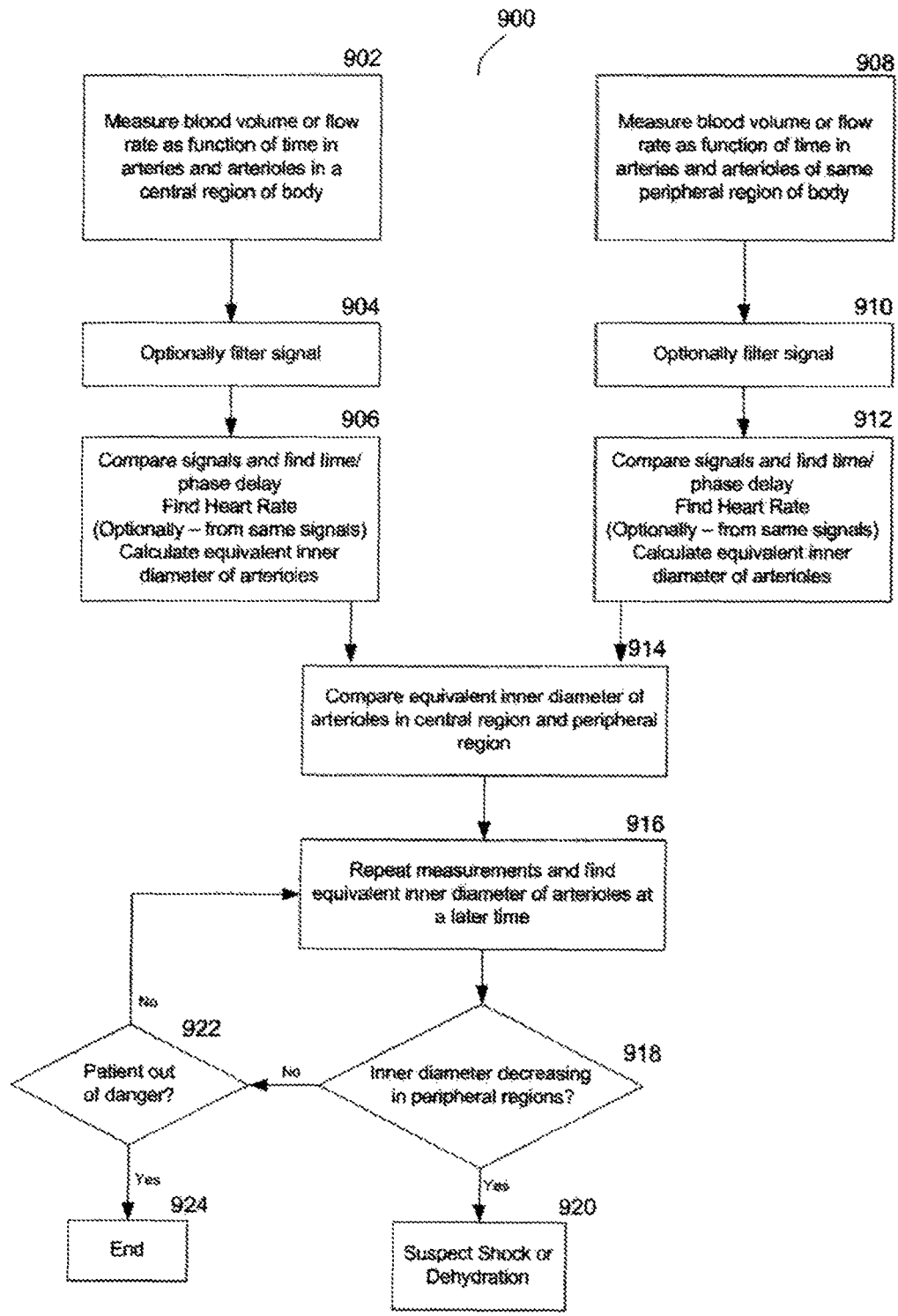
FIG. 9 is a flowchart for a method of evaluating shock or dehydration in a patient, by finding differences in the equivalent inner diameter of arterioles branching off from small arteries, for peripheral and central part of the patient's body, and optionally monitoring changes in those differences over time, according to an exemplary embodiment of the invention.

FIG. 9 shows a flowchart 900, for a method of assessing shock or dehydration in a patient, from their vasoconstrictive effect, using the method of FIG. 5. Shock can be an indication of hidden internal bleeding in a trauma patient, and having a way to detect it early or to continuously monitor for it in a non-invasive way, using inexpensive equipment that could be carried in an ambulance or used routinely in an emergency room, could potentially save lives. The method of flowchart 900 uses the fact that, in shock or in dehydration, peripheral blood vessels tend to undergo vasoconstriction first, in order to preserve the volume of blood in the central region of the body, and the area of vasoconstriction increases, towards the center of the body, the trunk, if shock or dehydration persists. Using the method of FIG. 5 to detect a trend in vasoconstriction, in time and in different parts of the body, may be easier than using the method of FIG. 5 to assess a degree of vasoconstriction absolutely, at only one time and one part of the body.

At 902, a quantity that serves as an indication of a pressure wave in blood vessels, such as blood volume or blood flow rate, is measured in a larger branching blood vessels and in the smaller blood vessels that branch off from it, for example using one of the systems shown in FIG. 1 or 4, in a central part of the body of a patient. Signals from these measurements are optionally low-pass filtered, at 904, and optionally detrended. A time difference between the two signals, for the larger and smaller blood vessels, is found at 906 and, being coupled with obtained at the same time heart rate value, enables to estimate an equivalent inner diameter value of smaller blood vessels. At 908, measurements are made, similar to the measurements made at 902, but for one or more peripheral parts of the body. The signals from these measurements are optionally filtered at 910, and a time difference between the larger and smaller blood vessels is found at 912 and, being coupled with obtained at the same time heart rate value, also enables to estimate an equivalent inner diameter value of smaller blood vessels from other peripheral part of body. Optionally, similar measurements are made and an equivalent inner diameter values are found for several different peripheral parts of the body that are at increasing distances from the central part of the body, in order to determine whether vasoconstriction increases with distance from the central part of the body, as would be expected in a patient exhibiting shock of dehydration. Measurements at multiple locations can also be made to reduce error.

At 914, the equivalent inner diameter values are compared in the central part of the body and in the one or more peripheral parts. Optionally, an estimation is made from these measurements at a single time as to whether the patient is exhibiting increasing vasoconstriction going further out from the central part of the body. At 916, the measurements are repeated, and the equivalent inner diameter values found, at a later time. If, at 918, it is found that the equivalent inner diameter value is decreasing with time, indicating increased vasoconstriction, in peripheral regions of the body more than in the central part of the body, and especially if this trend is strongest in the most peripheral regions, this is an indication that the patient may be suffering from shock or dehydration, which are diagnosed, at least tentatively, at 920.

Optionally, if the patient is being monitored for these conditions, then medical personnel are alerted at this time, for example through a cell phone or Bluetooth device, or by sounding an alarm in a room where the patient is located. If no such trend of increasing vasoconstriction in peripheral parts of the body is found, and if patient is judged to be out of danger at 922, then the procedure is ended at 924. If the patient is not judged to be out of danger, then measurements continue to be made, and equivalent inner diameter values found, at later times, at 916.

Sometimes it may be useful or necessary to measure changes in diameter of arterioles at same time with measurement of other important physiologic parameter.

As an example, we will describe embodiment, combining properties of standard pulse-oximeter with ability to measure changes in diameter of arterioles at same measurement region.

Figure 16:
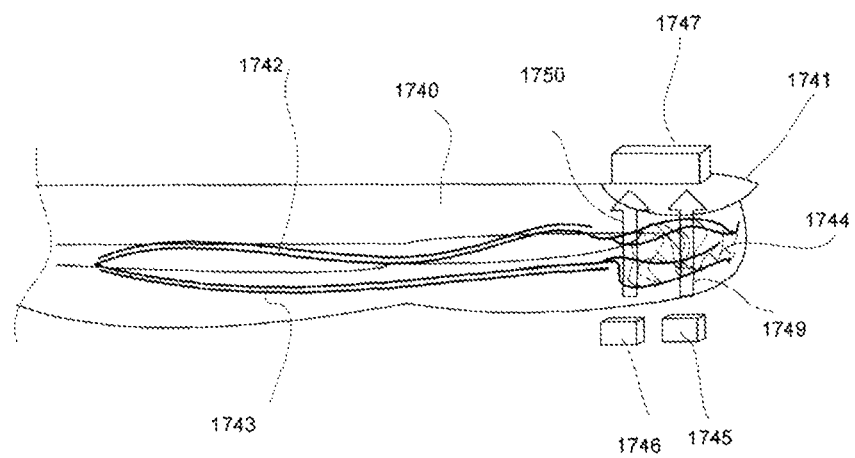
FIG. 16 illustrates standard embodiment of transition pulse-oximeter.

Said embodiment is based on principle of standard transmittance pulse-oximeter (see FIG. 16). Here optical module, including, as usual, infrared optical transmitter 1746, red light optical transmitter 1745 and photodetector 1747 are placed at two sides of finger before fingertip, where photodetector 1747 is placed upon nail 1741 and two said optical transmitters are placed at an opposite side of finger.

Digital artery 1743 does not come to same part of finger, being branched there to small arterioles. So as digital vein 1742 is represent before also.

Optical beams 1750 and 1749, irradiating by said optical transmitters 1746 and 1745 consequently, are collected at photodetector 1747 after direct diffusive drift through vascular bath 44, consisting mainly of arterioles, venules and capillary.

Waveforms of both signals, collected on photodetector 1747, are processed by well-known principle of "ratio of ratios" and, after calibration by predefined numerical table, final result of oxygen saturation is provided.

Figure 17:
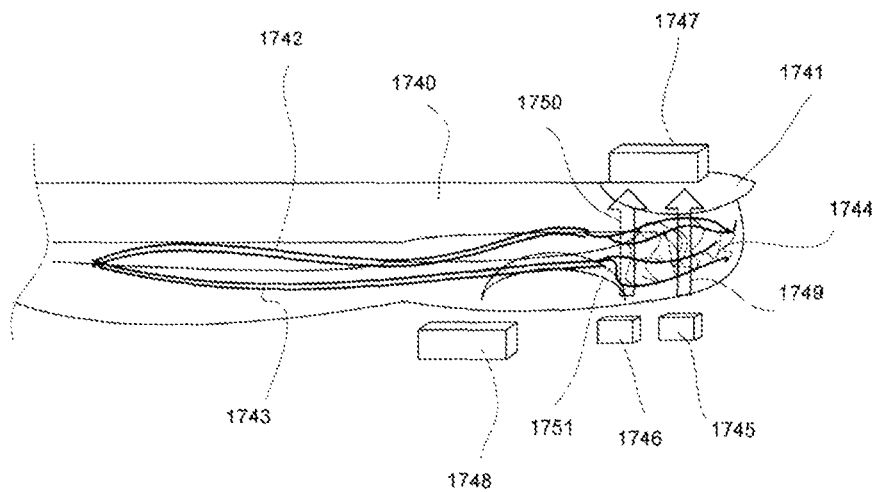
FIG. 17 illustrates a transition pulse-oximeter with ability to monitor changes of arteriole's equivalent inner diameter in measured region of tissue.

On FIG. 17 additional photodetector 1748 is placed at same side as optical transmitters, at a distance from infrared transmitter enough to have diffusion "canoe" arc 1751 between said photodetector 1748 and infrared optical transmitter 1746, that passing inside finger tissue and reaching digital artery 1742. It is easy to see that waveform, collected by said photodetector 1748, is not collected from same measurement region, like waveforms, collected by photodetector 1747.

Here measurements of blood flow from different types of vessels are achieved from different parts of body organ (finger), and might be even from different fingers of same palm, but still related to same peripheral part of blood vessel tree (hand region here), as it was claimed in present invention.

From FIG. 17 we may provide both blood oxygen saturation and peripheral vasoconstriction level measuring functions in one device. It is easy to understand that same result may be achieved on basis of reflective pulse-oximeter, where, for example, one only photodetector enables to collect waveform signal from two optical transmitters, providing oximetric measurements from same region of small arterioles and from an additional optical transmitter, placed to distance from said photodetector, adapted to build the "canoe" arc with depth for measurement of artery from same blood vessel tree.

Figure 18:
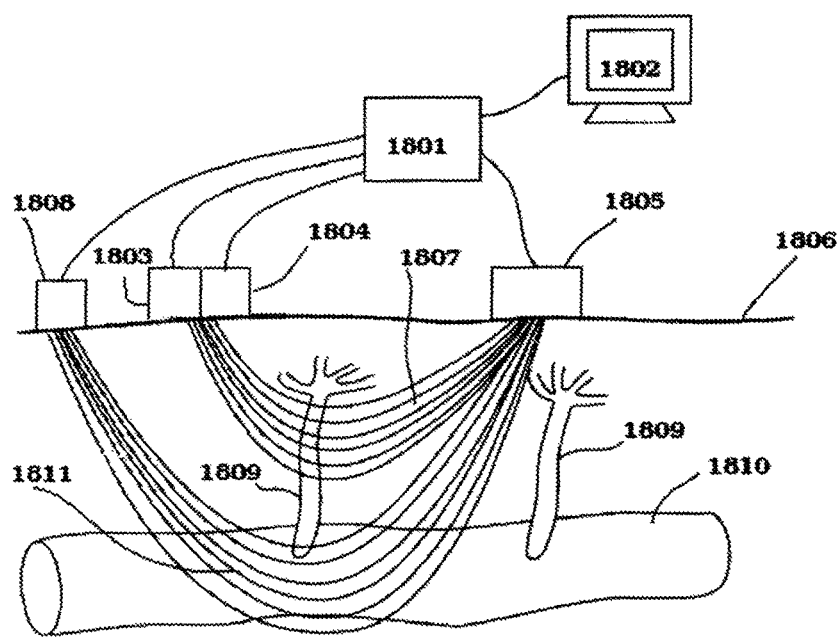
FIG. 18 illustrates a reflection pulse-oximeter embodiment with ability to monitor changes of arteriole's equivalent inner diameter in measured region of tissue.

Such a configuration is illustrated by an example device on FIG. 18, where optical signals from light sources 1803 and 1804 with wavelengths, adapted for measurements of oxygen saturation in blood, placed at nearly same place and same distance from light detector 1805 close to the surface of tissue 1806 so, that their trajectory in measured tissue passes through region, including mainly arterioles 1809, branched off from small arteries 1810, displaced deeper, then said arterioles.

Thus controller 1801 enables to collect biological signals, which may be used to find oxygen saturation value in blood of measured region.

Additional light source 1808 is places at longer distance from light detector 1805, then said light sources 1803 and 1804. Said longer distance enables to light detector 1805 to collect optical signal from said additional light source 1808 through deeper optical arc trajectory 1811, that passes mainly through said small arteries 1810, thus blood volume of said small arteries prevails on blood volume of arterioles 1809, branched off from them.

Being also collected by controller 1801 from same light detector 1805, this additional signal may be compared by processing unit 1802 to at least one of signals, initiated by light sources 1803 and 1804 in order to find time difference between them and, in coupling with obtained at the same time heart rate value to estimate equivalent inner diameter of arterioles.

Wide range of perspective measurements, related to indicating or monitoring changes for equivalent inner diameter value of arterioles, may be done in same principle manner also for internal organs, by mean, for example, of acoustic/ultrasonic techniques.

Figure 19:
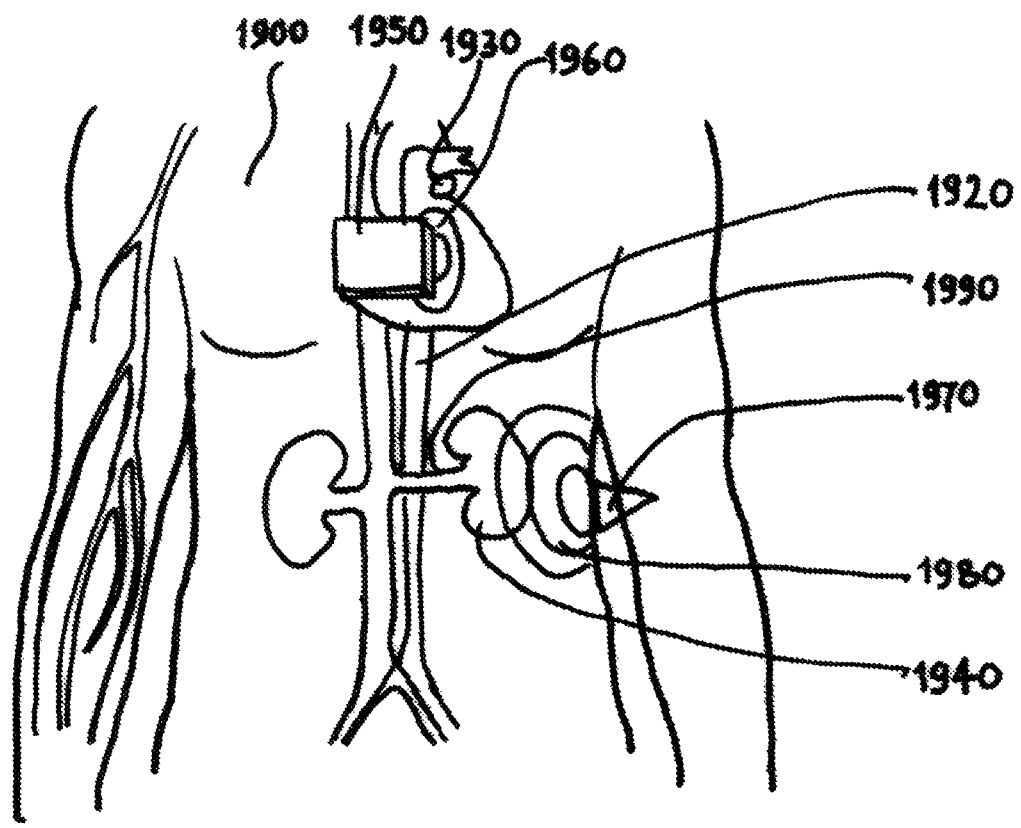
FIG. 19 illustrates a reflection acoustic/ultrasonic embodiment with ability to monitor changes of arteriole's equivalent inner diameter in the region of kidney.

An exemplary configuration for such measurements is illustrated in FIG. 19, where acoustic or ultrasonic signals 1980 from sensor 1970 propagates on predefined distance in human body 1900 to tissues of kidney 1940 and their scattered energy, being modulated by periodic blood flow pulsations in small arteries and arterioles of said kidney, is registered by said sensor.

The sensor 1970 may comprise a preference of Doppler measurements. Sensor 1970 is non-invasive. Alternatively, sensor 1970 can be used on an internal surface of the subject's body, for example on a surface of an internal organ during surgery, in an endoscopic procedure or during long term internal monitoring or monitoring of internal organ, for example in transplantation of kidney, inside nasal passage, in the gastrointestinal tract, in the ear, or in the urethra, or on the kidney. Alternatively, sensors like 1970 and described here-after 1950 can combine non-invasive and invasive parts.

The kidney 1940 is being supplied by Renal artery 1990, branched from Celiac artery 1920.

Celiac artery is a continuation artery of Aortic Arch 1930, providing heart pressure waves of blood. In order to measure time or phase differences between blood flow of said big arteries and small arteries of kidney 1940, it may be reasonable to measure the second signal from region of Aortic Arch 1930. The sensor 1950, which is intended for it, may be of active or passive type. I.e. it may be an ultrasonic sensor, irradiating acoustic energy to the measured region 1930 and the scattered part of said energy, being modulated by periodic blood flow pulsations in Aortic Arch, will registered by said sensor.

By another way, the sensor 1950 of passive type may, for example, simply register natural acoustic signals 1960 of heart contractions, thus providing same time-dependent data for the second signal as well.

A general principle of this invention may be embodied also by means of sensors, based on measurement of electrical signals or electrical impedance.

Really, conductivity of larger blood vessels and smaller blood vessels, like arterioles, branching off of them is changing proportional to propagation process of blood pressure waves there. Thus time or phase differences between signals may be measured by sensors of said type also.

Figure 20:
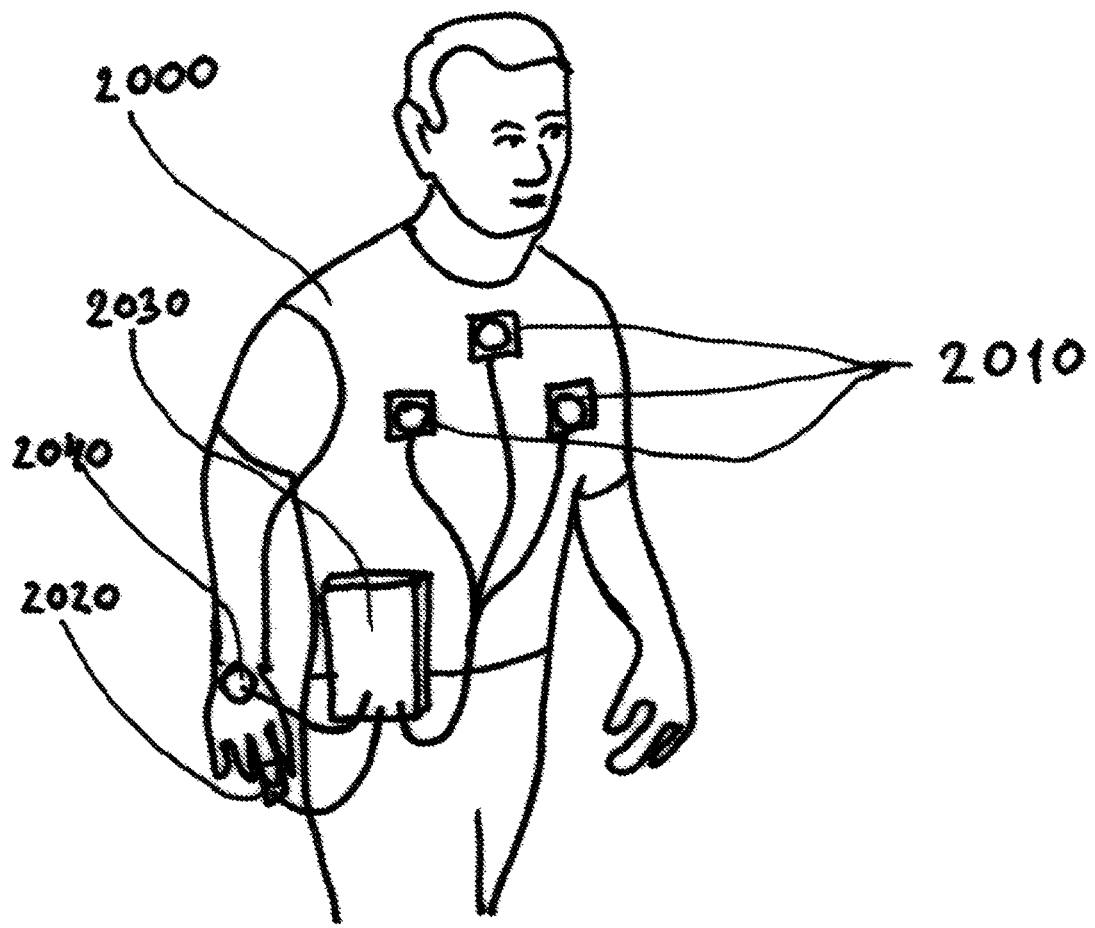
FIG. 20 illustrates an exemplary embodiment with ability to monitor changes of arteriole's equivalent inner diameter also by means of electrical sensors.

An exemplary configuration of such embodiment is described on FIG. 20.

Here ECG-like electrical sensors 2010 are attached to heart region of the human body 2000 and measure electrical signals, concurrent to heart contraction activity.

Said sensors 2010 may optionally or alternatively measure changes in conductivity of Aortic Arch region due to blood pressure wave propagation there.

The sensor 2020 may measure electric conductivity of peripheral blood circulation, changing because pulsation of peripheral blood pressure, or may be, for example, of photoplethysmographic type, thus measuring signal, proportional to changes of blood volume in preselected region of peripheral tissues. And additional sensor 2040 may be placed relatively close to sensor 2020 to measure a signal from local small arteries. It enables to obtain time difference (PWTT, transit time) between arterial signals from sensor 2010 and from sensor 2040, which will be separated here from influence of artery-arteriole's transient time. Said obtained transit time optionally may be used, for example, to get additional information about parameters or possible pathologies, relating to functionality of arterial system, locating between said sensors 2010 and 2040, or, optionally or alternatively relating to common cardiovascular conditions of measured subject.

Said separation of between time differences of PWTT type from common time/phase differences, measured from signals of sensors 2010 and 2020, thus may improve estimation of arterioles transient time and equivalent inner diameter of arterioles in measured region 2020.

As it was explained in previous embodiments, processing of time or phase differences (arterioles transient time) between these signals by processor 2030, together with concurrently measured value of heart rate of the subject enables to indicate changes in equivalent inner diameter of peripheral arterioles and, optionally or alternatively, changes of blood viscosity in measured region.

Various embodiments and aspects of the present invention as delineated hereinabove and as claimed in the claims section below find experimental support in the following examples.

The term "equivalent inner diameter" means for blood vessel an equivalent diameter of inner duct of blood vessel, where "equivalent inner diameter" of blood vessels in measured region means the inner diameter of equal non-branched circular ducts or blood vessels plurality in measured region that gives the same pressure loss as a numerically equal plurality of real, non-circular ducts or blood vessels with natural dispersion of their geometric, branching and physiologic parameters in a live biologic tissue.

The term "systemic circulation" means the general circulation, carrying oxygenated blood from the left ventricle to the body tissues, and returning venous blood to the right atrium.

"Peripheral part of systemic circulation" means here peripheral blood vessels and blood vessels, supplying tissues of internal organs i.e. hand, arm, finger, foot, leg, kidney, lever, intestine, eye, brain, lungs and so on and being branched from same larger artery from central part of the systemic circulation.

"Peripheral blood vessels" means those which are not in the core of the body and not those which supply skeletal muscles and the most common example is the blood vessels of the skin.

The term "Blood flow" means the continuous and pulsate running of blood in the cardiovascular system.

The term "transient time" means time difference between at least two pulse wave related signals, which is mainly created during pulse wave propagation from a lower flow impedance of artery-like blood vessels to a higher flow impedance of arteriole-like blood vessels.

The terms "branching", "branching from", "branching off from" mean branching off of one blood vessel directly or indirectly from another.

The terms "branching directly", "branching directly from", "directly branching off from" mean direct branching off of one blood vessel from another. The term "correlative to" means "proportional to or a function of".

The terms "comprises", "comprising", "includes", "including", "having" and their conjugates mean "including but not limited to".

The term "consisting of" means "including and limited to".

The term "concurrently" includes at least one of means "operating or occurring at the same time", "running parallel", "meeting or intersecting in a point" and "acting in conjunction".

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

EXAMPLES

Reference is now made to the following example from physiological trials, which together with the above descriptions illustrates a sample from series of experiments for experimental confirmation of current invention in a non-limiting fashion.

A test was made, using a PPG system similar to that described in FIG. 1, and the method of FIG. 5, on the forearm of subjects, before and after immersing the arm in cold water. The measurements were performed according to the following protocol:

1. The time difference was measured between green and near infrared PPG signals with measuring depth of 3-4 mm and 8-9 mm under the skin consequently, on the forearm of the subject closer to the wrist, for 20 seconds, before immersing the subject's arm in cold water.

2. The subject's forearm was immersed in cold water with temperature of 18 degrees C., and the surface temperature of the forearm was measured once a minute with a non-contact IR sensor approved by the FDA for measuring body temperature, until it had fallen to 22 degrees C.

3. The area of the forearm to be measured was quickly dried, and the time difference was measured again for 20 seconds.

4. The surface temperature of the forearm, the time difference, and the uncertainty in the time difference, were recorded before and after cooling, and the room temperature was recorded.

5. The procedure was repeated at intervals of at least 24 hours with approximately same values of Heart Rate.

6. Heart Rate was measured around 105 BPM during all represented measurements. Several results from the experiment are shown below in Table 1:

TABLE 1

Test data for time delay before and after cooling subject's arm

| Tw = 18° C. | | Data before cooling | | Data after cooling | | |
| --- | --- | --- | --- | --- | --- | --- |
| # | Time | Temp., ° C. Before | Time Delay Before, ms | Temp., ° C. After | Time Delay After, ms | Room Temperature, C. |
| 1 | 06:35:00 PM | 34.9 | 56.9 | 24.0-25.6 | 80.53 | 19 |
| 2 | 08:14:00 PM | 35.2 | 38.8 | 23.5-25.5 | 91.11 | 18 |
| 3 | 06:15:00 PM | 35.1 | 26.84 | 23.8-25.1 | 84.56 | 18 |
| 4 | 03:25:00 PM | 34.9 | 32.14 | 23.2-24.2 | 83.45 | 18 |
| 5 | 05:22:00 PM | 35.6 | 34 | 24.5-25.1 | 73.73 | 18 |
| 6 | 05:34:00 PM | 35.2 | 19.47 | 23.8-25.2 | 82.37 | 18 |

The time shift before the arm was cooled had a mean value of 34 milliseconds and a standard deviation of 14 milliseconds, with most of that standard deviation due to uncertainty in the measured value. After the arm was cooled, the time shift had a mean value 83 milliseconds, with a standard deviation of 6 milliseconds.

The difference in time shift before and after cooling the arm is very statistically significant, and shows that the effect of narrowing the blood vessels, which would increase the time shift, is most powerful reason of time shift changes.

By relating measured data about time differences and heart rate value to plot on FIG. 13, we may find initial inner diameter of arteriole as varied from 26 to 30 micrometers before local cooling and after local cooling was decreased to about 18 micrometers that is reasonable change of reasonable values.

Here well-known physiological phenomena of thermal vasoconstriction was demonstrated directly, without involving any other measuring equipment, regularly used by skilled in the art in such a case (1 D or 2D Doppler Flowmeter ets).

Although the invention has been described in conjunction with specific embodiments thereof, it is evident that many alternatives, modifications and variations will be apparent to those skilled in the art.

Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Vitaly A. Kalion, Ivan V. Kazachkov, and Yuri I. Shmakov Rheology of Complex Fluids and Blood Flows, Stockholm 2004.
2. David Elad and Shmuel Einav, PHYSICAL AND FLOW PROPERTIES OF BLOOD. Standard Handbook Of Biomedical Engineering And Design
3. Mette S. Olufsen ON DERIVING LUMPED MODELS FOR BLOOD FLOW AND PRESSURE IN THE SYSTEMIC ARTERIES. MATHEMATICAL BIOSCIENCES AND ENGINEERING Volume 1, Number 1, June 2004
4. Alan C. Burton Physiology and Biophysics of Circulation. 2-nd Edition, 1972
5. Mette S. Olufsen, Ali Nadim MATHEMATICAL BIOSCIENCES AND ENGINEERING Volume 1, Number 1, June 2004
6. J. Keener and J. Sneyd, Mathematical Physiology, vol. 8th of Interdisciplinary Applied Mathematics New York, N.Y.: Springer Verlag, 1998.
7. Simulating of Human Cardiovascular System and Blood Vessel Obstruction Using Lumped Method, Mohammad Reza Mirzaee, Omid Ghasemalizadeh, and Bahar Firoozabadi, World Academy of Science, Engineering and Technology 41 2008
8. A multi-compartment vascular model for inferring arteriole dilation and cerebral metabolic changes during functional activation Theodore J. Huppert1,2, Monica S. Allen3, Heval Benav1, Anna Devor1,4, Phil Jones1, Anders Dale4, and David A. Boas1,5
1 Athinoula A. Martinos Center for Biomedical Imaging Massachusetts General Hospital, Charlestown, Mass. 02129, USA
9. Pulse pressure and arterial elasticity S. E. GREENWALD From the Department of Histopathology and Morbid Anatomy, Barts and The London Queen Mary's School of Medicine and Dentistry, Royal London Hospital, London, UK
10. WINDKESSEL MODEL ANALYSIS IN MATLAB Ing. Martin HLAVÁČ, Doctoral Degree Programme (3) Dept. of Biomedical Engineering, FEEC, BUT
11. A new method for assessing arteriolar diameter and hemodynamic resistance using image analysis of vessel lumen Karel Tym1,1,2 Donald Anderson,2 Darcy Lidington,1,2 and Hanif M. Ladak *Am J Physiol Heart Circ Physiol* 284: H1721-H1728, 2003
12. Cardiovascular Physiology Concepts, Richard E. Klabunde, PhD, Revised Apr. 1, 2007, http://cyphysiology.com/Blood%20Pressure/BP021.htm
13. Fundus camera-based retinal laser doppler velocimeter, U.S. Pat. No. 4,402,601
14. Holographic laser Doppler ophthalmoscopy, M. Simonutti, M. Paques, J. A. Sahel, M. Gross, B. Samson, C. Magnain,4 and M. Atlan4,
1 Institut de la Vision, Institut National de la Santé et de la Recherche Médicale (INSERM)-101, UMR-S 968, rue de Tolbiac, 75654 Paris Cedex 13, France
15. Combined effects of pulsatile flow and dynamic curvature on wall shear stress in a coronary artery bifurcation model, I. V. Pivkin1, P. D. Richardson2, D. H. Laidlaw3 and G. E. Karniadakis1 ¤ Brown University Oct. 29, 2003

16. Validation of a one-dimensional model of the systemic arterial tree, Philippe Reymond, Fabrice Merenda, Fabienne Perren, Daniel Rüfenacht and Nikos Stergiopulos, *Am J Physiol Heart Circ Physiol* 297:H208-H222, 2009. First published 8 May 2009;
17. Evidence of a Cerebrovascular Postarteriole Windkessel With Delayed Compliance Joseph B Mandeville*,[†], John J A Marota*,[‡] C Ayata[§], Greg Zaharchuk*,[†], Michael A Moskowitz[§], Bruce R Rosen*,[†] and Robert M Weisskoff*,[†] *Journal of Cerebral Blood Flow & Metabolism* (1999) 19, 679-689;
18. A multi-compartment vascular model for inferring arteriole dilation and cerebral metabolic changes during functional activation Theodore J. Huppert1,2, Monica S. Allen3, Heval Benav1, Anna Devor1,4, Phil Jones1, Anders Dale4, and David A. Boas1,5 *J Cereb Blood Flow Metab.* 2007 June; 27(6): 1262-1279. doi:10.1038/sj.jcbfm.9600435.
19. A vascular anatomical network model of the spatiotemporal response to brain activation David A. Boas, Stephanie R. Jones, Anna Devor, Theodore J. Huppert, and Anders M. Dale Neuroimage. Author manuscript; available in PMC Apr. 15, 2009.

20. http://www.nihonkohden.com/tech/escco/principle.html#principle

What is claimed is:

1. A method for estimation of inner diameter of arterioles in measured body part, the method comprising:
    obtaining a first pressure wave signal from a first tissue volume beneath the surface of a part of a subject's body, containing blood vessels; wherein contribution in the first signal from artery-like blood vessels predominates over contribution from arteriole-like blood vessels;
    obtaining a second pressure wave signal from a second tissue volume beneath the surface of the part of the subject's body, containing blood vessels; wherein contribution in the second signal from arteriole-like blood vessels predominates over contribution from artery-like blood vessels;
    obtaining at least one concurrent heart rate value;
    finding time delay values between the first signal and the second signal; and using said at least one value of the time delay values and said at least one heart rate value to calculate an equivalent inner diameter of said arterioles.

2. The method of claim 1, wherein said first tissue volume is from a characteristic depth of arteries beneath the surface of said part of subject's body.

3. The method according to claim 2, wherein said characteristic depth of said first tissue volume is between 7 and 9 mm under the skin of the subject's body.

4. The method according to claim 1, wherein the time delay between said first signal and said second signal is within a range from 9.23 to 93.94 milliseconds.

5. The method according to claim 1, wherein the time delay between said first signal and said second signal is in range from 19.47 to 91.11 milliseconds.

6. The method according to claim 1, wherein said first signal is obtained by a light of infrared color.

7. The method according to claim 1, wherein said first and second volumes are related to the same peripheral body part.

8. The method according to claim 1, wherein estimation of an equivalent inner diameter of said arterioles also uses blood viscosity value of measured subject.

9. The method according to claim 1, further comprising:
    obtaining information about at least one parameter having a physiological influence on the subject over time;
    finding correlation between changes over time of said at least one parameter and changes over time in said estimated equivalent inner diameter value of arterioles.

10. The method according to claim 9, wherein said parameter represents a substance entering to subject body.

11. The method according to claim 9, wherein said parameter is a behavioral parameter of the subject.

12. The method according to claim 1, wherein estimation equivalent inner diameter value of arterioles is done, after all said first and second signals are collected.

13. The method of claim 1, wherein said second tissue volume is from characteristic depth of arterioles beneath the surface of said part of subject's body.

14. The method according to claim 13, wherein said characteristic depth of said second tissue volume is between 3 and 4 mm under the skin of the subject's body.

15. The method according to claim 1, wherein said second signal is obtained by a light of green color.

* * * * *